US009277950B2

(12) United States Patent
Buttermann

(10) Patent No.: US 9,277,950 B2
(45) Date of Patent: Mar. 8, 2016

(54) LOW-PROFILE, UNIPLANAR BONE SCREW

(75) Inventor: Glenn R. Buttermann, Mahtomedi, MN (US)

(73) Assignee: Dynamic Spine, LLC, Mahtomedi, MN (US)

( * ) Notice: Subject to any disclaimer, the term of this patent is extended or adjusted under 35 U.S.C. 154(b) by 239 days.

(21) Appl. No.: 13/702,854

(22) PCT Filed: Jun. 9, 2011

(86) PCT No.: PCT/US2011/039760
§ 371 (c)(1),
(2), (4) Date: Feb. 14, 2013

(87) PCT Pub. No.: WO2011/156573
PCT Pub. Date: Dec. 15, 2011

(65) Prior Publication Data
US 2013/0184770 A1 Jul. 18, 2013

Related U.S. Application Data

(60) Provisional application No. 61/353,586, filed on Jun. 10, 2010, provisional application No. 61/394,274, filed on Oct. 18, 2010.

(51) Int. Cl.
*A61B 17/04* (2006.01)
*A61B 17/86* (2006.01)
*A61F 2/08* (2006.01)
*A61B 17/70* (2006.01)

(52) U.S. Cl.
CPC ......... *A61B 17/8605* (2013.01); *A61B 17/7038* (2013.01); *A61B 17/7041* (2013.01); *A61B 17/704* (2013.01)

(58) Field of Classification Search
USPC .......................................... 606/305
See application file for complete search history.

(56) References Cited

U.S. PATENT DOCUMENTS

| 945,213 A | 1/1910 | Blackburn |
| 1,766,546 A | 6/1930 | Roos |
| 2,537,322 A | 1/1951 | Wazenberg |

(Continued)

FOREIGN PATENT DOCUMENTS

| DE | 28 21 678 A1 | 11/1979 |
| FR | 2782911 A | 3/2000 |

(Continued)

OTHER PUBLICATIONS

Non-Final Office Action dated Aug. 19, 2014, received in U.S. Appl. No. 13/028,161.

(Continued)

*Primary Examiner* — Sameh Boles
(74) *Attorney, Agent, or Firm* — Foley & Lardner LLP

(57) ABSTRACT

A bone screw that is a low-profile, uniplanar bone screw is provided. The bone screw is for adjusting a position of a rod. The bone screw includes a main body, a rocker and a rod-securing element. The main body has a shaft with a threaded part. The rocker is coupled to and moveable relative to the main body. The rocker is configured to at least partially receive the rod. The rod-securing element is configured to secure the rod between the rocker and the rod-securing element and relative to the main body. The rod-securing element includes a fulcrum serving as an axis of rotation about which the rod rotates.

22 Claims, 27 Drawing Sheets

(56) References Cited

U.S. PATENT DOCUMENTS

| | | |
|---|---|---|
| 2,543,550 A | 2/1951 | Kneeland |
| 2,589,520 A | 3/1952 | Wallenius |
| 2,722,440 A | 11/1955 | Barton |
| 2,824,913 A | 2/1958 | Taylor |
| 4,085,744 A | 4/1978 | Lewis et al. |
| 4,361,141 A | 11/1982 | Tanner |
| 4,364,381 A | 12/1982 | Sher et al. |
| 4,409,968 A | 10/1983 | Drummond |
| 4,411,259 A | 10/1983 | Drummond |
| 4,422,451 A | 12/1983 | Kalamchi |
| 4,531,522 A | 7/1985 | Bedi et al. |
| 4,611,582 A | 9/1986 | Duff |
| 4,619,447 A | 10/1986 | Blake |
| 4,702,447 A | 10/1987 | Westwood, III |
| 4,823,636 A | 4/1989 | Suska |
| 4,852,841 A | 8/1989 | Sebring |
| 4,901,964 A | 2/1990 | McConnell |
| 4,950,270 A | 8/1990 | Bowman et al. |
| 5,007,909 A | 4/1991 | Rogozinski |
| 5,030,235 A | 7/1991 | Campbell, Jr. |
| 5,074,864 A | 12/1991 | Cozad et al. |
| 5,096,150 A | 3/1992 | Westwood |
| 5,112,332 A | 5/1992 | Cozad et al. |
| 5,116,334 A | 5/1992 | Cozad et al. |
| 5,147,359 A | 9/1992 | Cozad et al. |
| 5,190,543 A | 3/1993 | Schlapfer |
| 5,261,908 A | 11/1993 | Campbell, Jr. |
| 5,290,289 A | 3/1994 | Sanders et al. |
| 5,330,472 A | 7/1994 | Metz-Stavenhagen |
| 5,334,203 A | 8/1994 | Wagner |
| 5,344,422 A | 9/1994 | Frigg |
| 5,352,225 A | 10/1994 | Yuan et al. |
| 5,380,326 A | 1/1995 | Lin |
| 5,413,576 A | 5/1995 | Rivard |
| 5,415,659 A | 5/1995 | Lee et al. |
| 5,423,857 A | 6/1995 | Rosenman et al. |
| 5,507,747 A | 4/1996 | Yuan et al. |
| 5,520,689 A | 5/1996 | Schlapfer et al. |
| 5,586,983 A | 12/1996 | Sanders et al. |
| 5,630,816 A | 5/1997 | Kambin |
| 5,632,744 A | 5/1997 | Campbell, Jr. |
| 5,662,648 A | 9/1997 | Faccioli et al. |
| 5,676,665 A | 10/1997 | Bryan |
| 5,688,273 A | 11/1997 | Errico et al. |
| 5,688,274 A | 11/1997 | Errico et al. |
| 5,689,864 A | 11/1997 | White |
| 5,697,650 A | 12/1997 | Brown |
| 5,733,284 A | 3/1998 | Martin |
| 5,800,548 A | 9/1998 | Martin et al. |
| 6,053,917 A | 4/2000 | Sherman et al. |
| 6,136,000 A | 10/2000 | Louis et al. |
| 6,352,537 B1 | 3/2002 | Strnad |
| 6,375,656 B1 | 4/2002 | Faure |
| 6,387,097 B1 | 5/2002 | Alby |
| 6,547,789 B1 | 4/2003 | Ventre et al. |
| 6,589,243 B1 | 7/2003 | Viart et al. |
| 6,626,909 B2 | 9/2003 | Chin |
| 6,660,007 B2 | 12/2003 | Khanna |
| 6,719,795 B1 | 4/2004 | Cornwall et al. |
| 6,860,884 B2 | 3/2005 | Shirado et al. |
| 6,926,242 B2 | 8/2005 | Hall |
| 7,011,659 B2 | 3/2006 | Lewis et al. |
| 7,029,472 B1 | 4/2006 | Fortin |
| 7,137,986 B2 | 11/2006 | Troxell et al. |
| 7,249,399 B2 | 7/2007 | Taylor |
| 7,264,620 B2 | 9/2007 | Taylor |
| 7,338,490 B2 | 3/2008 | Ogilvie et al. |
| 7,614,173 B2 | 11/2009 | Kim |
| 7,635,365 B2 | 12/2009 | Ellis et al. |
| 7,666,210 B2 | 2/2010 | Franck et al. |
| 7,695,501 B2 | 4/2010 | Ellis et al. |
| 7,703,358 B2 | 4/2010 | Ubinana Felix |
| 7,713,284 B2 | 5/2010 | Crofford |
| 7,717,938 B2 | 5/2010 | Kim et al. |
| 7,883,532 B2 | 2/2011 | Biscup et al. |
| 7,901,436 B2 | 3/2011 | Baccelli |
| 7,922,746 B2 | 4/2011 | Miller |
| 7,927,355 B2 | 4/2011 | Berrevoets et al. |
| 7,927,357 B2 | 4/2011 | Sacher et al. |
| 7,942,908 B2 | 5/2011 | Sacher et al. |
| 7,966,703 B2 | 6/2011 | Ubinana Felix |
| 7,980,521 B2 | 7/2011 | Harr et al. |
| 8,025,678 B2 | 9/2011 | Reynolds et al. |
| 8,025,683 B2 | 9/2011 | Morrison |
| 8,043,337 B2 | 10/2011 | Klyce et al. |
| 8,048,166 B2 | 11/2011 | Brown et al. |
| 8,051,515 B1 | 11/2011 | Kring |
| 8,057,472 B2 | 11/2011 | Walker et al. |
| 8,075,597 B2 | 12/2011 | Stahurski et al. |
| 8,080,037 B2 | 12/2011 | Butler et al. |
| 8,080,046 B2 | 12/2011 | Suddaby |
| 8,083,780 B2 | 12/2011 | McClellan et al. |
| 8,105,366 B2 | 1/2012 | Null et al. |
| 8,172,875 B2 | 5/2012 | Taylor |
| 8,172,882 B2 | 5/2012 | Klyce et al. |
| 8,172,887 B2 | 5/2012 | Gabele |
| 8,177,823 B2 | 5/2012 | Lake et al. |
| 8,197,515 B2 | 6/2012 | Levy et al. |
| 8,197,543 B2 | 6/2012 | Wang |
| 8,226,689 B2 | 7/2012 | Jones et al. |
| 8,231,655 B2 | 7/2012 | Stinson et al. |
| 8,241,334 B2 | 8/2012 | Butler et al. |
| 8,246,660 B2 | 8/2012 | Boris et al. |
| 8,292,924 B2 | 10/2012 | Neary et al. |
| 8,298,275 B2 | 10/2012 | Rezach |
| 8,313,514 B2 | 11/2012 | Puno |
| 8,430,917 B2 | 4/2013 | Rezach |
| 8,790,380 B2 | 7/2014 | Buttermann |
| 8,915,962 B1 | 12/2014 | Suddaby |
| 2002/0013585 A1 | 1/2002 | Gournay et al. |
| 2002/0019633 A1 | 2/2002 | Ray |
| 2002/0095156 A1 | 7/2002 | Kuras et al. |
| 2002/0169451 A1 | 11/2002 | Yeh |
| 2003/0004511 A1 | 1/2003 | Ferree |
| 2003/0032959 A1 | 2/2003 | Yeh |
| 2003/0045876 A1 | 3/2003 | Stahurski |
| 2003/0080267 A1 | 5/2003 | Eslick |
| 2003/0083659 A1 | 5/2003 | Lin et al. |
| 2003/0088251 A1 | 5/2003 | Braun et al. |
| 2003/0109881 A1 | 6/2003 | Shirado et al. |
| 2003/0109882 A1 | 6/2003 | Shirado et al. |
| 2003/0125738 A1 | 7/2003 | Khanna |
| 2003/0125740 A1 | 7/2003 | Khanna |
| 2003/0130659 A1 | 7/2003 | Haider |
| 2003/0187437 A1 | 10/2003 | Ginsburg |
| 2004/0030388 A1 | 2/2004 | Null et al. |
| 2004/0055429 A1 | 3/2004 | Winkler |
| 2004/0064140 A1 | 4/2004 | Taylor et al. |
| 2004/0087948 A1 | 5/2004 | Suddaby |
| 2004/0111091 A1 | 6/2004 | Ogilvie et al. |
| 2004/0186472 A1 | 9/2004 | Lewis et al. |
| 2005/0131412 A1 | 6/2005 | Olevsky et al. |
| 2005/0171539 A1 | 8/2005 | Braun et al. |
| 2005/0228377 A1 | 10/2005 | Chao et al. |
| 2005/0251138 A1 | 11/2005 | Boris et al. |
| 2005/0267475 A1 | 12/2005 | Miller, III |
| 2005/0267480 A1 | 12/2005 | Suddaby |
| 2005/0273100 A1 | 12/2005 | Taylor |
| 2006/0036241 A1 | 2/2006 | Siegal |
| 2006/0058790 A1 | 3/2006 | Carl et al. |
| 2006/0084990 A1 | 4/2006 | Gournay et al. |
| 2006/0116687 A1 | 6/2006 | Miller et al. |
| 2006/0155279 A1 | 7/2006 | Ogilvie |
| 2006/0229615 A1 | 10/2006 | Abdou |
| 2006/0229616 A1 | 10/2006 | Albert et al. |
| 2006/0235391 A1 | 10/2006 | Sutterlin, III |
| 2006/0241601 A1 | 10/2006 | Trautwein et al. |
| 2006/0247626 A1 | 11/2006 | Taylor et al. |
| 2006/0271193 A1 | 11/2006 | Hartmann et al. |
| 2006/0293663 A1 | 12/2006 | Walkenhorst et al. |
| 2007/0016189 A1 | 1/2007 | Lake et al. |
| 2007/0072459 A1 | 3/2007 | Stahurski et al. |
| 2007/0083201 A1 | 4/2007 | Jones et al. |
| 2007/0118118 A1 | 5/2007 | Kwak et al. |

(56) References Cited

U.S. PATENT DOCUMENTS

| | | |
|---|---|---|
| 2007/0123883 A1 | 5/2007 | Ellis et al. |
| 2007/0225713 A1 | 9/2007 | Altarac et al. |
| 2007/0239161 A1 | 10/2007 | Giger et al. |
| 2007/0276384 A1 | 11/2007 | Spratt |
| 2008/0033436 A1 | 2/2008 | Song et al. |
| 2008/0077144 A1 | 3/2008 | Crofford |
| 2008/0103512 A1 | 5/2008 | Gately |
| 2008/0114401 A1 | 5/2008 | Liu et al. |
| 2008/0177315 A1 | 7/2008 | Usher |
| 2008/0228225 A1 | 9/2008 | Trautwein et al. |
| 2008/0234733 A1 | 9/2008 | Scrantz et al. |
| 2008/0234766 A1 | 9/2008 | Henderson et al. |
| 2008/0294200 A1 | 11/2008 | Kohm et al. |
| 2008/0306551 A1 | 12/2008 | Sanders et al. |
| 2009/0018584 A1 | 1/2009 | Henderson et al. |
| 2009/0030457 A1 | 1/2009 | Janowski et al. |
| 2009/0030462 A1 | 1/2009 | Buttermann |
| 2009/0062869 A1 | 3/2009 | Claverie et al. |
| 2009/0105766 A1 | 4/2009 | Thompson et al. |
| 2009/0112263 A1 | 4/2009 | Pool et al. |
| 2009/0118774 A1 | 5/2009 | Miller, III |
| 2009/0118775 A1 | 5/2009 | Burke |
| 2009/0163920 A1 | 6/2009 | Hochschuler et al. |
| 2009/0177230 A1 | 7/2009 | Henderson et al. |
| 2009/0198277 A1 | 8/2009 | Gordon et al. |
| 2009/0248090 A1 | 10/2009 | Gordon et al. |
| 2009/0270929 A1 | 10/2009 | Suddaby |
| 2009/0287253 A1 | 11/2009 | Felix et al. |
| 2010/0057127 A1 | 3/2010 | McGuire et al. |
| 2010/0069960 A1 | 3/2010 | Chaput |
| 2010/0094303 A1 | 4/2010 | Chang et al. |
| 2010/0121381 A1 | 5/2010 | Berta et al. |
| 2010/0137913 A1 | 6/2010 | Khatchadourian et al. |
| 2010/0152575 A1 | 6/2010 | Henderson et al. |
| 2010/0160979 A1 | 6/2010 | Tornier |
| 2010/0179597 A1 | 7/2010 | Henderson et al. |
| 2010/0198274 A1 | 8/2010 | Yeung et al. |
| 2010/0217271 A1 | 8/2010 | Pool et al. |
| 2010/0222822 A1 | 9/2010 | Farris et al. |
| 2010/0241230 A1 | 9/2010 | Mazzuca et al. |
| 2010/0249842 A1 | 9/2010 | Mir |
| 2010/0274291 A1 | 10/2010 | McClellan et al. |
| 2010/0292739 A1 | 11/2010 | Schwab |
| 2010/0305616 A1 | 12/2010 | Carbone |
| 2011/0106163 A1 | 5/2011 | Hochschuler et al. |
| 2011/0111929 A1 | 5/2011 | Allison et al. |
| 2011/0137353 A1 | 6/2011 | Buttermann |
| 2011/0144694 A1 | 6/2011 | Laeng et al. |
| 2011/0160779 A1 | 6/2011 | Schlaepfer et al. |
| 2011/0178552 A1 | 7/2011 | Biscup et al. |
| 2011/0184463 A1 | 7/2011 | Schwend |
| 2011/0251643 A1 | 10/2011 | Miladi |
| 2011/0257690 A1* | 10/2011 | Rezach .......... 606/302 |
| 2011/0288592 A1 | 11/2011 | McKinley |
| 2011/0313323 A1 | 12/2011 | Henderson et al. |
| 2012/0016420 A1 | 1/2012 | Naraghi |
| 2012/0035656 A1 | 2/2012 | Pool et al. |
| 2012/0035661 A1 | 2/2012 | Pool et al. |
| 2012/0047690 A1 | 3/2012 | Ginocchio |
| 2012/0083851 A1 | 4/2012 | Felix et al. |
| 2012/0088380 A1 | 4/2012 | Smith |
| 2012/0209328 A1 | 8/2012 | Alamin et al. |
| 2012/0271352 A1 | 10/2012 | Schulze et al. |
| 2012/0271354 A1 | 10/2012 | Baccelli et al. |
| 2012/0283780 A1 | 11/2012 | Ludwig et al. |
| 2013/0041410 A1 | 2/2013 | Hestad et al. |
| 2013/0046352 A1 | 2/2013 | McClintock |
| 2013/0131738 A1 | 5/2013 | Powell et al. |
| 2013/0218208 A1 | 8/2013 | Khoury |
| 2013/0231704 A1 | 9/2013 | Larroque-Lahitette |
| 2013/0274807 A1 | 10/2013 | Prajapati |
| 2013/0304129 A1 | 11/2013 | Hawkins et al. |
| 2014/0135853 A1 | 5/2014 | Reisberg |
| 2014/0214087 A1 | 7/2014 | Wahl et al. |
| 2014/0222074 A1 | 8/2014 | Rathbun et al. |
| 2014/0236234 A1 | 8/2014 | Kroll et al. |
| 2014/0257488 A1 | 9/2014 | Alheidt et al. |
| 2014/0277147 A1 | 9/2014 | Alexander et al. |
| 2014/0336705 A1 | 11/2014 | Butterman |
| 2014/0343612 A1 | 11/2014 | Rezach et al. |
| 2015/0025574 A1 | 1/2015 | Mackall |
| 2015/0032158 A1 | 1/2015 | Khajavi et al. |
| 2015/0032159 A1 | 1/2015 | Beger et al. |

FOREIGN PATENT DOCUMENTS

| | | |
|---|---|---|
| FR | 2892617 A | 5/2007 |
| WO | WO-90/12553 A | 11/1990 |
| WO | WO-93/25161 A | 12/1993 |
| WO | WO 9729707 A | 11/1996 |
| WO | WO-97/29707 A | 8/1997 |
| WO | WO-2004/019757 A2 | 3/2004 |
| WO | WO-2005/044152 A1 | 5/2005 |
| WO | WO-2011/133690 A2 | 10/2011 |
| WO | WO-2011/156573 A1 | 12/2011 |

OTHER PUBLICATIONS

European Office Action dated Oct. 25, 2011 as received in corresponding European Patent Application No. 08743411.4, 5 pages.

European Office Action dated Sep. 23, 2010 as received in corresponding European Patent Application No. 08743411.4, 3 pages.

International Search Report and Written Opinion dated Jun. 29, 2012 as received in corresponding PCT Application No. PCT/US2012/024887.

International Search Report and Written Opinion dated Oct. 4, 2011 as received in corresponding PCT Application No. PCT/US2011/039760, 13 pages.

International Search Report mailed Nov. 12, 2008 in PCT/US2008/005532, 5 pages.

Kim, Won Joong, et al. "The Influence of Fixation Rigidity on Intervertebral Joints—An Experimental Comparison between a Rigid and a Flexible System", J Korean Neurosurg Soc, vol. 37, 2005, pp. 364-369.

Office Action received in connection with U.S. Appl. No. 13/028,161 dated Dec. 20, 2012.

Patent Examination Report received in connection with related Australian application No. AU2008279798 dtd Nov. 14, 2012.

US Office Action dated Aug. 10, 2011 as received in corresponding U.S. Appl. No. 12/149,406, 12 pages.

US Office Action dated Sep. 24, 2012 as received in corresponding U.S. Appl. No. 12/149,403.

US Office Action received in U.S. Appl. No. 12/149,403; DTD Feb. 22, 2011.

Supplementary European Search Report in corresponding European Application No. 11793147.7 dated Oct. 10, 2014, 7 pages.

International Search Report and Written Opinion in PCT/US2013/027386 dated Apr. 26, 2013.

Australian Office Action dated Jan. 15, 2014 received in corresponding AU Application No. 2011264818.

Notice of Allowance received in related U.S. Appl. No. 12/149,403 dated Mar. 14, 2014.

Final Office Action dated Aug. 14, 2013, as received in co-pending U.S. Appl. No. 13/028,161.

US Non-Final Office Action issued in U.S. Appl. No. 14/444,860 dated Mar. 12, 2015.

US Notice of Allowance issued in U.S. Appl. No. 13/028,161 dated Mar. 24, 2015.

Patent Examination Report No. 2 received in corresponding Australian application No. 2011264818 dated Mar. 5, 2015, 4 pages.

Office Action issued in co-pending Canadian Application No. 2,694,437 mailed May 13, 2014.

Office Action issued in co-pending Canadian Patent Application No. 2,694,437 mailed Mar. 5, 2015.

Notice of Allowance dated Jun. 17, 2015 in U.S. Appl. No. 13/028,161, 11 pages.

Patent Examination Report No. 1 dated Aug. 6, 2015, recieved in corresponding Austrailian application No. 2012217924, 7 pages.

* cited by examiner

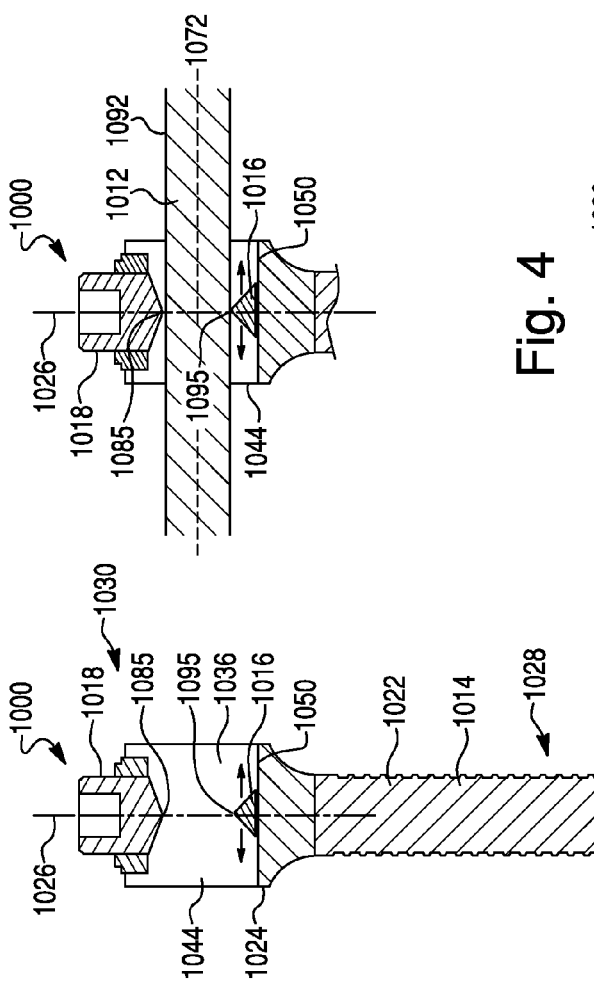
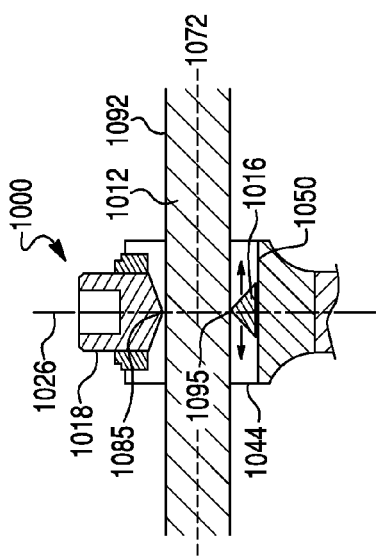
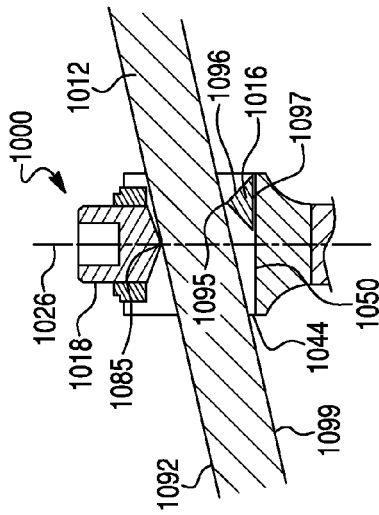
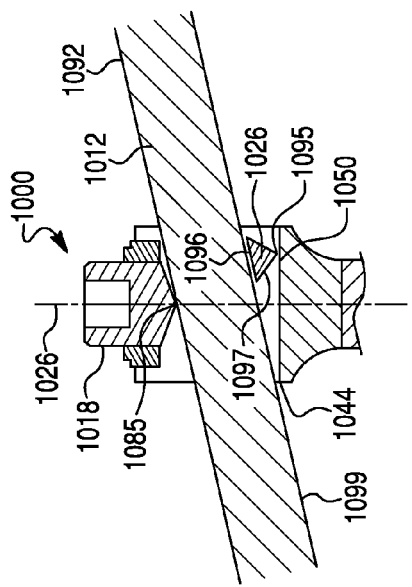
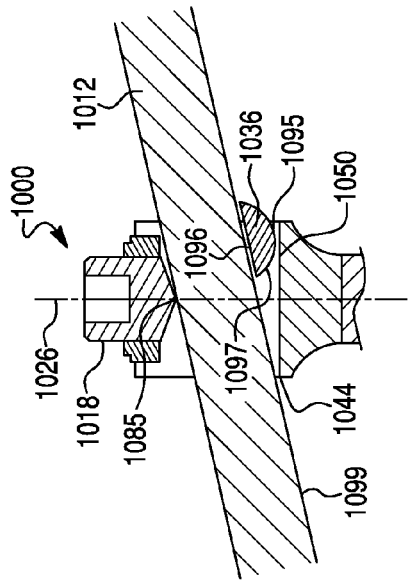

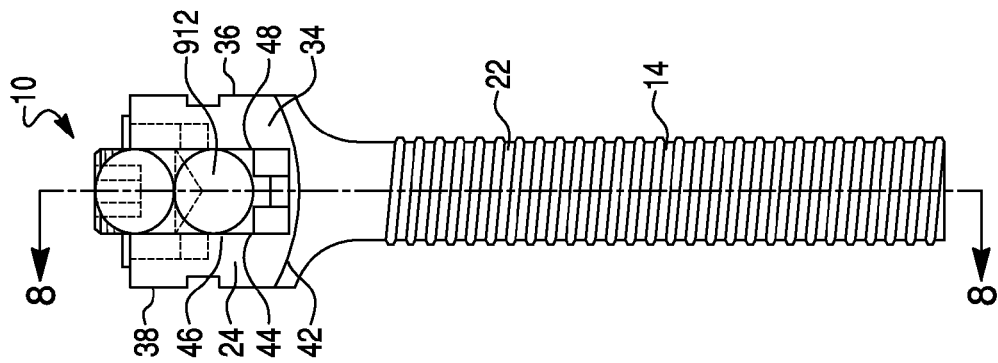
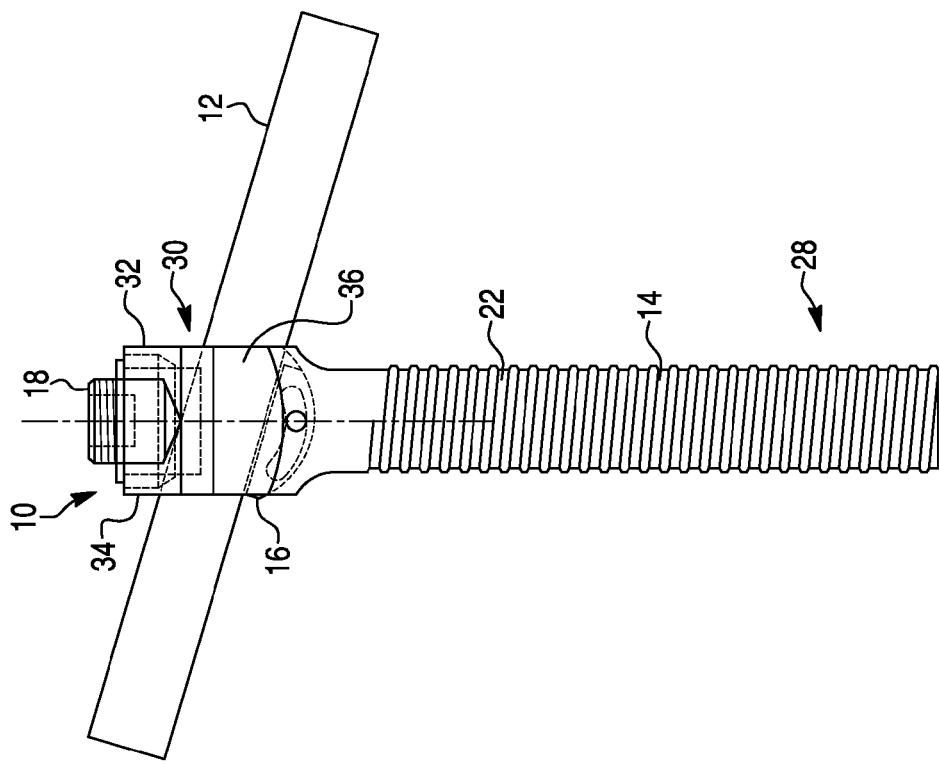

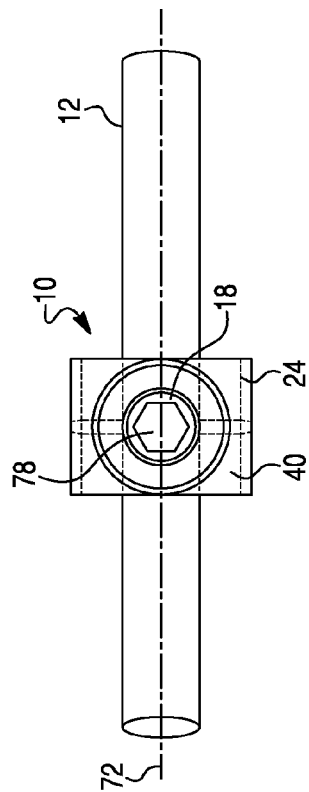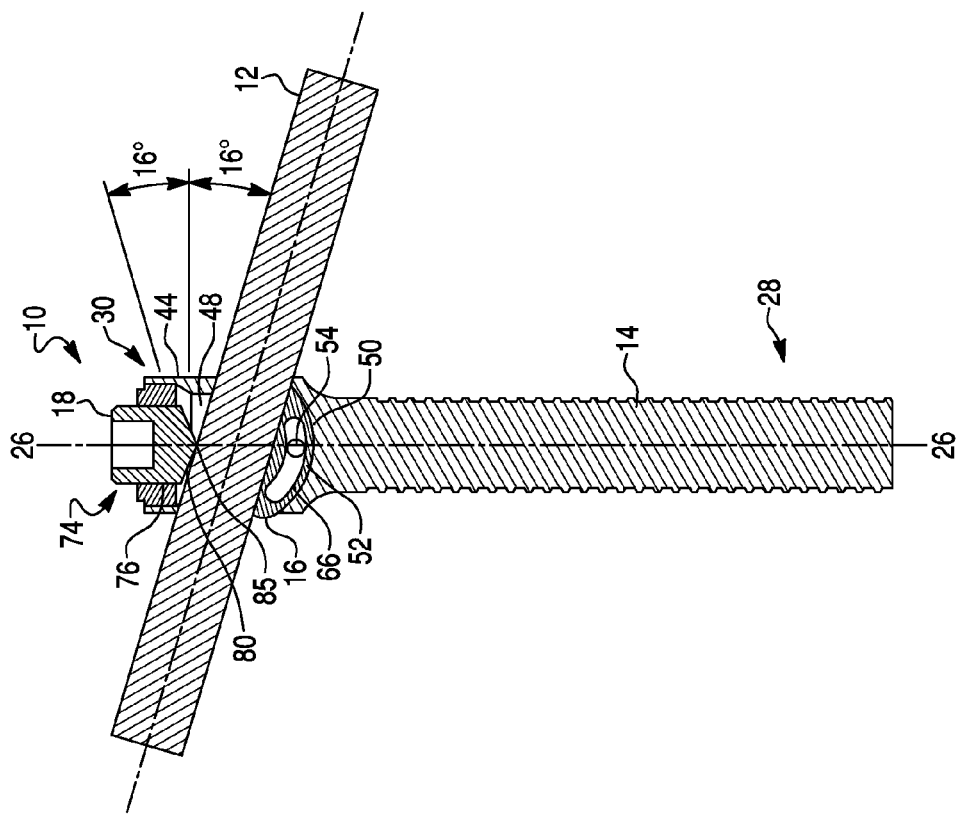

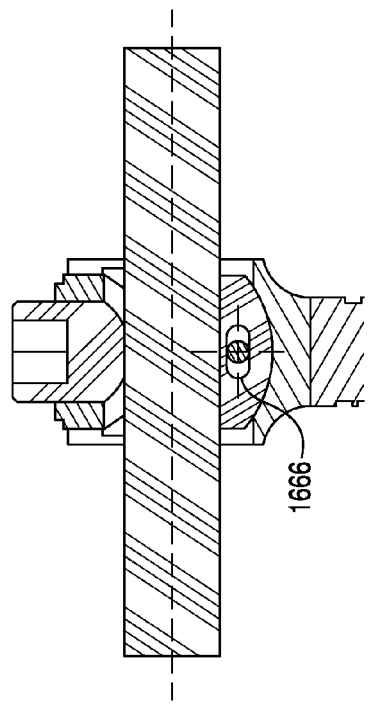
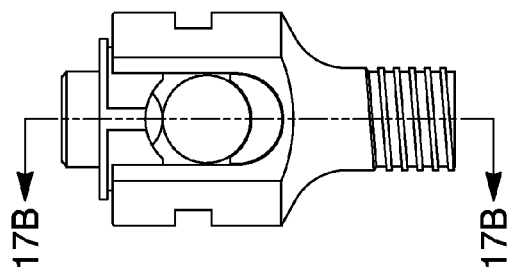
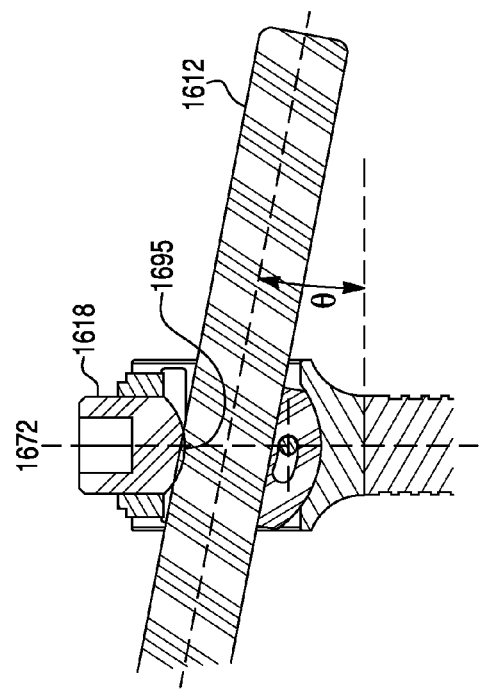

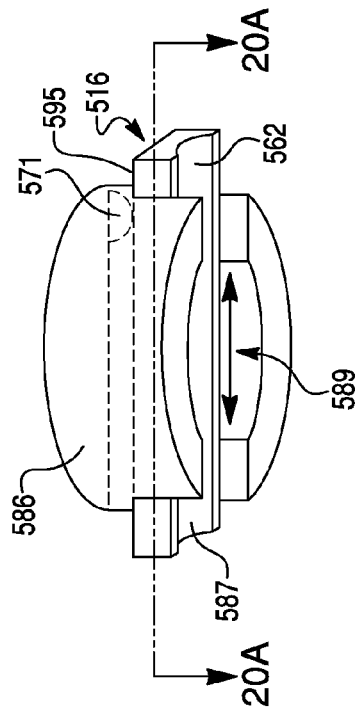
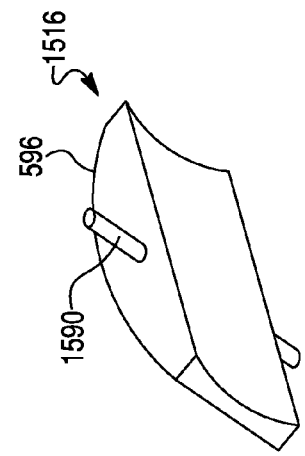
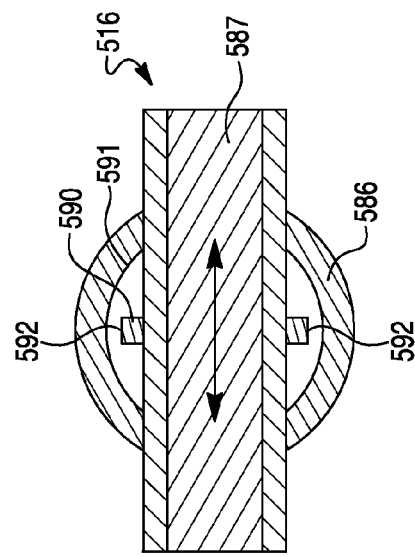
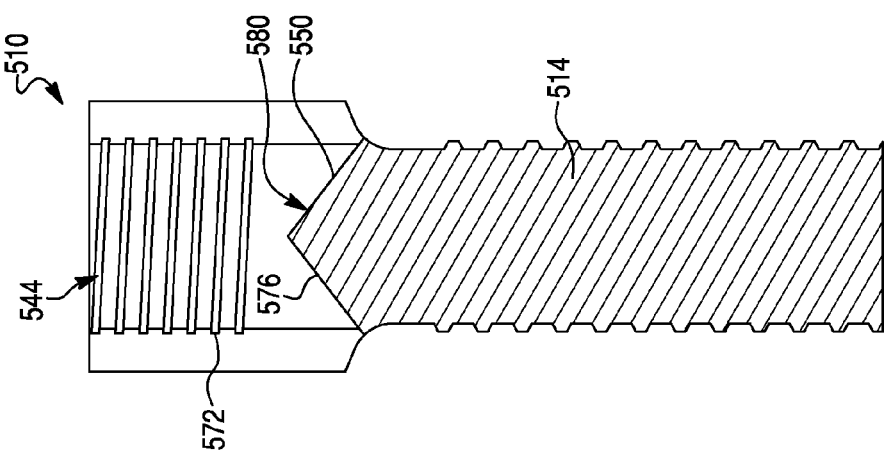

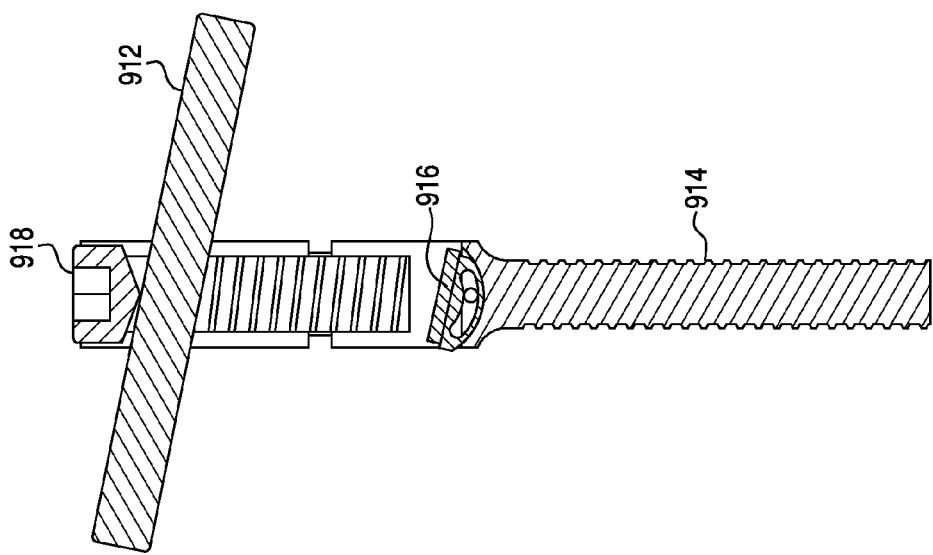
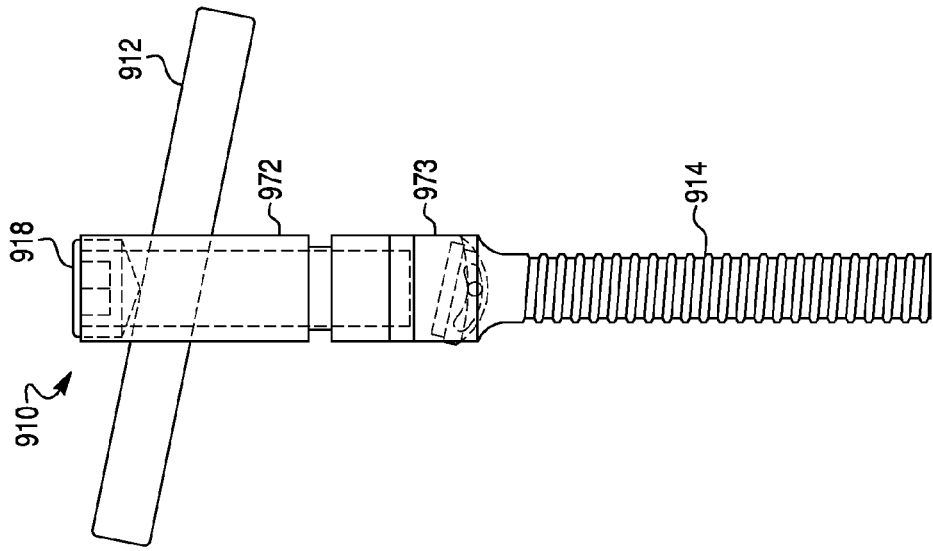
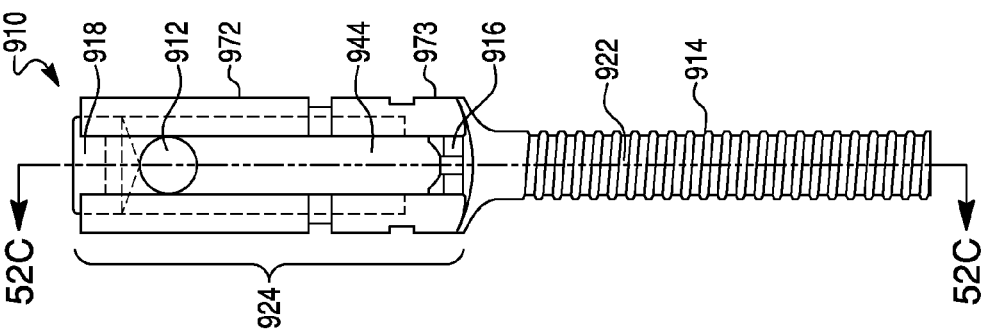
Fig. 52C
Fig. 52B
Fig. 52A

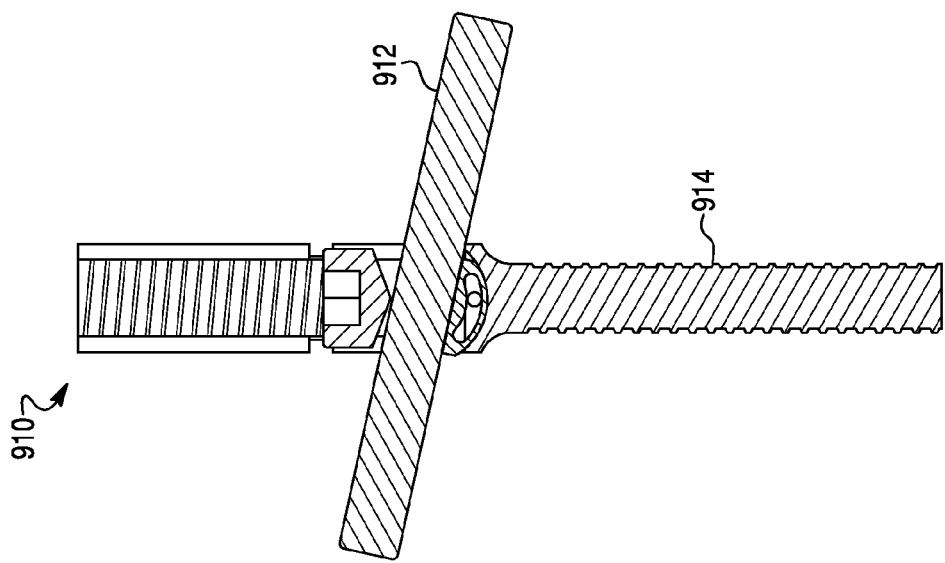
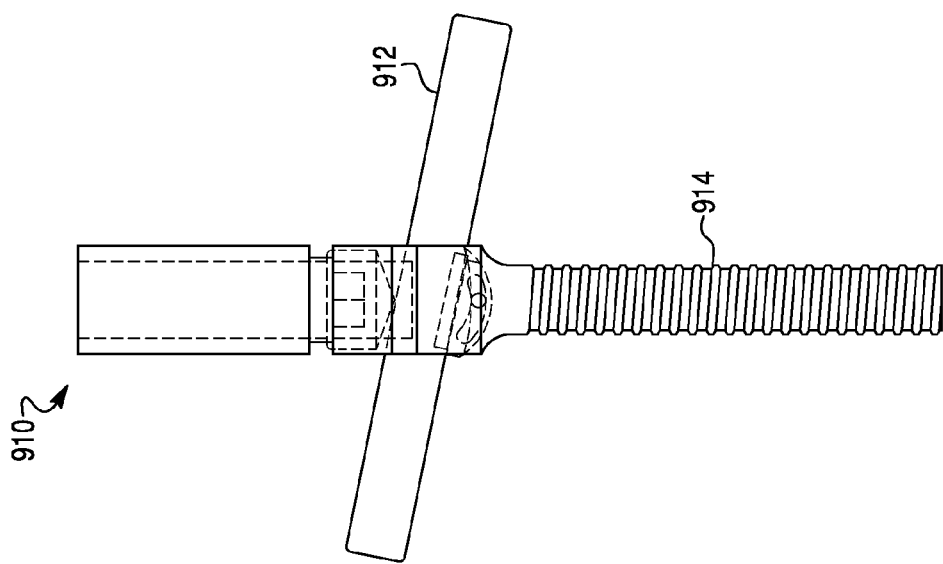
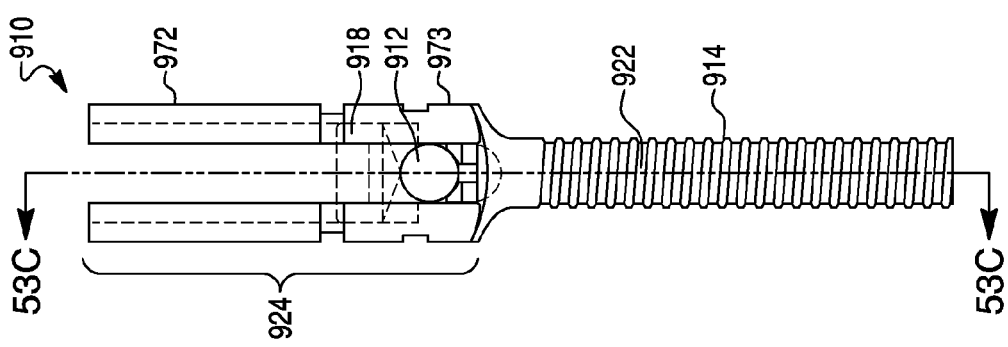

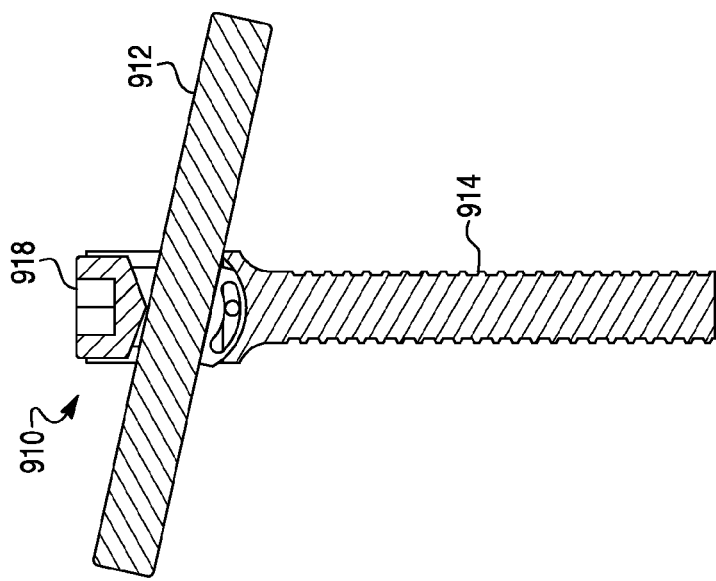
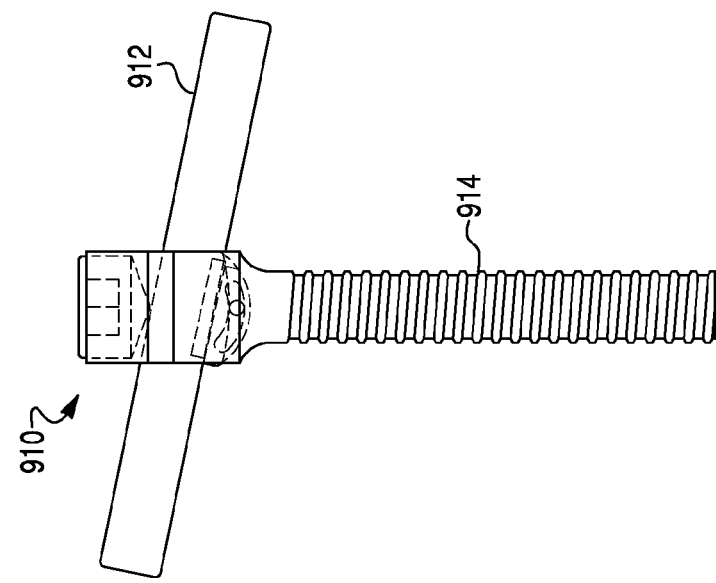
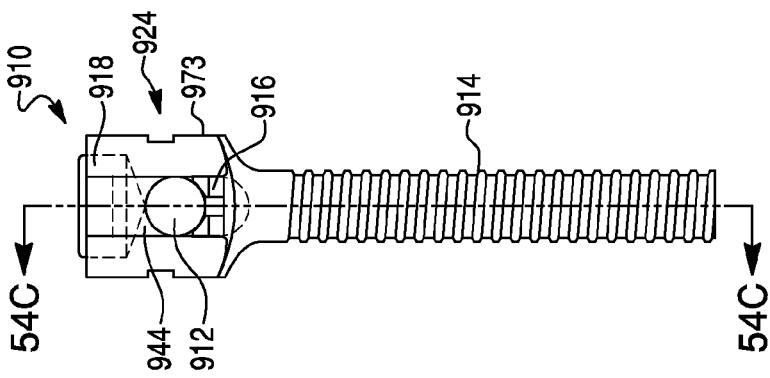

LOW-PROFILE, UNIPLANAR BONE SCREW

CROSS-REFERENCE TO RELATED PATENT APPLICATIONS

The present application is a National Stage of International Application No. PCT/US2011/039760 filed on Jun. 9, 2011, which claims priority to U.S. Provisional Application No. 61/353,586, filed Jun. 10, 2010, and U.S. Provisional Application No. 61/394,274, filed Oct. 18, 2010, the disclosures of which are all incorporated herein by reference in their entireties.

BACKGROUND

1. Field of Embodiments

The present embodiments relate generally to orthopedic devices. More specifically, the present embodiments relate to screws for orthopedic devices that are typically placed within or adjacent to vertebrae (e.g., pedicles). It should be noted, however, that the screws disclosed herein may also be used in other orthopedic applications. For example, the screws may be used for repositioning fractured bones relative to one another, or used in an external fixator for trauma patients.

2. Description of Related Art

During spinal fusion surgery, bone screws may be fixed to adjacent vertebrae and interconnected with rods that span the screws to stabilize the spine during the healing process. The screw heads typically include a slot that is intended to receive a rod. The rod may be at least partially secured within the slot by a cap or set screw. The rods interconnecting the bone screws may span one or more vertebral levels (e.g., one to two vertebral levels for a spinal fusion of a degenerative condition, eight to twelve vertebral levels for scoliosis, etc.).

During an orthopedic surgical procedure, a number of factors can impact bone screw placement and alignment. These factors include, but are not limited to, spinal curvatures, variations in patient anatomy, and small imprecisions in screw placement by the surgeon. It is generally desirable for bone screws to be configured to be adjustable in order to achieve a desired alignment. However, with conventional bone screws, greater adjustability of the bone screw typically means the screw is relatively bulky (e.g., relative to its less adjustable counterparts). Bulky bone screws can cause pain and irritation to some patients.

Bone screws can be classified as monoaxial, polyaxial or uniplanar based on their adjustability.

Monoaxial bone screws are the most simplistic and not particularly useful for accommodating screw placement and alignment. The screw head of a monoaxial screw allows adjustment to the rod only in the direction perpendicular to the longitudinal axis of the screw. When the rod is secured in the slot of the bone screw, the longitudinal axis of the rod is substantially perpendicular to (i.e., at a 90° angle to) the longitudinal axis of the bone screw.

Polyaxial screws are commonly used to overcome the variations in screw placement and alignment. The relationship between the screw axis and the rod axis can be variable but still be locked solidly in place (e.g., the screw head of a polyaxial screw may be configured to swivel approximately 20° off the screw axis). This adjustability allows rods to be connected to multiple screws that may be placed medial or lateral to one another and to provide for lordotic and kyphotic spinal alignments. Conventional polyaxial screws are larger and bulkier than monoaxial screws (e.g., because of the structures that provide for the screw head of a polyaxial screw to swivel).

Uniplanar screws have screw heads that may deviate from the screw axis but only in the plane of the slot for the rod; they typically do not adjust to medial or lateral rod positions (like polyaxial screws). This type of screw is more commonly used in scoliosis surgery where there may be a degree of cranial or caudal angulation (such as the sagittal plane of the spine), but there is little medial lateral screw placement deviation and the surgeon additionally needs rigid control of the screw to manipulate it in the coronal and axial plane of the spine. Similar to polyaxial screws, conventional uniplanar screws are large and bulky because of the configuration of their single plane swivel mechanism.

Because many scoliosis patients are children or smaller-sized adults and because many scoliosis fusions are performed in the kyphotic thoracic spine with less soft tissue coverage, the larger, bulkier polyaxial and uniplanar screws are often prominent and may cause pain and irritation to the patient. In some cases, the pain and irritation may rise to the level where a second surgery to remove the screws and rods is necessary.

A need exists for improved uniplanar bone screws, including bone screws that may address one or more of the above described disadvantages.

SUMMARY

One embodiment relates to a uniplanar bone screw for adjusting a position of a rod that comprises a main body, a rocker and a rod-securing element. The main body has a shaft with a threaded part. The rocker is coupled to and moveable relative to the main body. The rocker is configured to at least partially receive the rod. The rod-securing element is configured to secure the rod between the rocker and the rod-securing element and relative to the main body. The rod-securing element includes a fulcrum serving as an axis of rotation about which the rod rotates.

BRIEF DESCRIPTION OF THE DRAWINGS

These and other features, aspects and advantages of the disclosed embodiments will become apparent from the following description, appended claims and the accompanying exemplary embodiments shown in the drawings, which are briefly described below.

FIG. 1 is a cross-sectional view of a low-profile, uniplanar bone screw.

FIG. 2 is a cross-sectional view of a low-profile, uniplanar bone screw and rod.

FIG. 3 is a cross-sectional view of a low-profile, uniplanar bone screw and rod after a rocker moves.

FIG. 4 is a cross-sectional view of a low-profile, uniplanar bone screw after a rocker moves.

FIG. 5 is a cross-sectional view of a portion of a low-profile, uniplanar bone screw after a rocker moves.

FIG. 6 is a side plan view of a low-profile, uniplanar bone screw with a substantially curved base and interface to the rocker.

FIG. 7 is a front plan view of the low-profile, uniplanar bone screw of FIG. 6.

FIG. 8 is a cross-sectional view of the low-profile, uniplanar bone screw of FIG. 7 taken along line 8-8.

FIG. 9 is a top plan view of the low-profile, uniplanar bone screw of FIG. 6.

FIG. 17A is a front plan view of a low-profile, uniplanar bone screw.

FIG. 17B is a cross-sectional view of the low-profile, uniplanar bone screw of FIG. 17B taken along line 17B-17B.

FIG. 17C is a cross-sectional view of the low-profile, uniplanar bone screw of FIG. 17A with the rod rotated.

FIG. 18 is a cross-sectional view of a low-profile, uniplanar bone screw with a set screw, connector and a rocker removed.

FIG. 19 is a side view of the rocker and connector of the low-profile, uniplanar bone screw of FIG. 18.

FIG. 20A is a cross sectional view of the rocker and connector of FIG. 19 taken along line 20A-20A.

FIG. 20B is a perspective view of a rocker that could be used in the low-profile, uniplanar bone screw of FIG. 18.

FIG. 52A is a front view of a reduction screw.

FIG. 52B is a side view of the reduction screw of FIG. 52A.

FIG. 52C is a cross-sectional view of the reduction screw of FIG. 52A taken along line 52C-52C.

FIG. 53A is a front view of the reduction screw of FIG. 52A after a rod-securing element has moved a rod close to the shaft of the reduction screw.

FIG. 53B is a side view of the reduction screw of FIG. 52A after the rod-securing element has moved the rod close to the shaft of the reduction screw.

FIG. 53C is a cross-sectional view of the reduction screw of FIG. 53A taken along line 53C-53C.

FIG. 54A is a front view of the reduction screw of FIG. 52A after the top portion of the head has been removed.

FIG. 54B is a side view of the reduction screw of FIG. 52A after the top portion of the head has been removed.

FIG. 54C is a cross sectional view of FIG. 54A taken along line 54C-54C.

DETAILED DESCRIPTION

Figure 10:
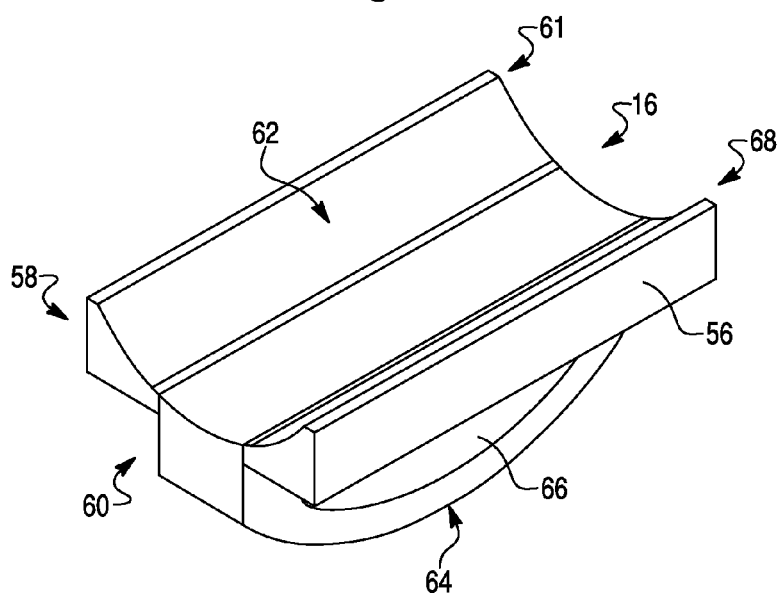
FIG. 10 is a perspective view of a rocker of the low-profile, uniplanar bone screw of FIG. 6.

Referring generally to the FIGURES, various embodiments of a bone screw that is a low-profile, uniplanar bone screw are shown. An effort has been made to use the same or like reference numbers throughout the drawings to refer to the same or like parts. The low-profile, uniplanar bone screw may be a reduction screw. The low-profile, uniplanar bone screw preferably includes a rocker. The rocker may be a swing or a sliding rod support where both the swing and the sliding rod support can translate and rotate around a common axis. The rocker is configured to be movable relative to the main body of the bone screw and, thereby, to provide for a rod disposed thereon to be adjustable at least within a single plane. Stated otherwise, by using the rocker, the head of the bone screw need not be movable in order to provide for uniplanar adjustment of the rod relative to the main body of the bone screw. Because the head of the bone screw does not need to be movable, the screw can be configured to be smaller and less bulky than a conventional uniplanar bone screw, thereby decreasing the likelihood of pain and irritation to a patient. As a result, the bone screw is low-profile. Accordingly, the rocker allows for the screw to be less bulky than conventional polyaxial and uniplanar bone screws, while still providing uniplanar movement of the rod relative to the bone screw (e.g., cranial or caudal angulation of the rod axis relative to the screw axis). In general, at least two low-profile, uniplanar bone screws are secured to the patient while a single rod is coupled to each bone screw.

Referring to FIGS. 1-9, a bone screw 10, 1000 having an elongated member shown as a rod 12, 1012 coupled thereto is shown. The bone screw 10, 1000 is a uniplanar bone screw that is configured to provide adjustability of a position of the rod 12, 1012 in a single plane, as will be discussed in more detail below. The bone screw 10, 1000 (e.g., a pedicle screw) includes a main body 14, 1014, a rocker 16, 1016 coupled to and moveable relative to the main 14, 1014 body and that is configured to at least partially receive the rod 12, 1012, and a rod-securing element 18, 1018 configured to secure the rod 12, 1012 between the rocker 16, 1016 and the rod-securing element 18, 1018 and relative to the main body 14, 1014. The rod-securing element 18, 1018 may be any suitable element, such as a set screw. The rod 12, 1012 is shown elongated along a longitudinal rod axis 72, 1072. The rocker 16, 1016 of FIGS. 1-9 is a sliding rod support.

The main body 14, 1014 includes a shaft 22, 1022 and a screw head 24, 1024 coupled to the shaft 22, 1022. The main body 14, 1014 generally defines a longitudinal screw axis 26, 1026 of the bone screw 10, 1000. The main body 14, 1014 of the bone screw 10, 1000 is configured to be secured to a person's spine (e.g., at a pedicle) to help couple the rod 12, 1012 to the patient's spine. The shaft 22, 1022 includes a threaded portion having a plurality of threads (the threaded portion of the shaft is not shown in FIGS. 5-9). The threaded portion of the shaft 22, 1022 is located at or proximate to a first end 28 of the bone screw 10, 1000 generally opposite a second end 30, 1030. The threaded portion is intended to be at least partially received within a bore (hole, cavity, etc.) formed in the person's spine. The threads of the threaded portion are configured to threadably engage the bore to secure the main body 14, 104 to the spine.

The screw head 24, 1024 is shown located at or proximate to the second end 30, 1030 of the bone screw 10, 1000. The head 24, 1024 is shown including a front side 32 (FIG. 6) generally opposite a rear side 34 (FIG. 6), a first side 36, 1036 generally opposite a second side 38 (FIG. 6), a top side 40 (FIG. 9) generally opposite a bottom side 42 (FIG. 7), and a slot 44, 1044. The slot 44, 1044 is configured to at least partially receive the rod 12, 1012. The slot 44, 1044 is shown extending a distance downward generally along the longitudinal screw axis 26, 1026 from the top side 40 of the head 24, 1024 toward the bottom side 42 of the head 24, 1024. The slot 44, 1044 is further shown extending through the head 24, 1024 from the front side 32 to the rear side 34 in a direction substantially perpendicular to the longitudinal screw axis 26, 1026. Typically, the rod 12, 1012 is positioned into the slot 44, 1044 by moving it from a position generally above the slot 44, 1044 downward. The extension of the slot 44, 1044 through the head 24, 1024 allows the rod 12, 1012 to extend therethrough (e.g., with the ends to either side). In this way, the rod 12, 1012 may be coupled to other bone screws. It should be noted that the slot 44, 1044 may have any size, shape or position suitable for at least partially receiving a rod.

The slot 44, 1044 is further configured to at least partially receive the sliding rod support 16, 1016, 1026, 1036 and to allow for movement of the sliding rod support 16, 1016, 1026, 1036 relative to the main body 14, 1014 (FIG. 8). Preferably the slot 44, 1044 and sliding rod support 16, 1016, 1026, 1036 are configured to facilitate maintaining the sliding rod support 16, 1016, 1026, 1036 in the slot 44, 1044. The slot 44, 1044 is generally defined by a first interior sidewall 46 (FIG. 7), a second interior sidewall 48 (FIG. 7), and a bottom surface 50 1050 that extends therebetween (i.e. the bottom surface 50, 1050 extends from the first interior sidewall 46 to the second interior sidewall 48). The bottom surface 50 is shown including a flat portion (FIGS. 1-5) or a generally curved portion, shown as a generally concave portion 52 (FIG. 8). The concave portion 52 is configured to facilitate movement of the sliding rod support 16, 1016, 1026, 1036 relative to the main body 14, 1014. The bottom surface 50, 1050 of the slot 44, 1044 supports the sliding rod support 16, 1016, 1026, 1036.

FIGS. 1-5 and 8 illustrate how the sliding rod support facilitates rotation of the rod about the rod-securing element 18, 1018 where the sliding rod support is configured to translate and/or rotate within the slot 1044. A tip 1085 of the rod-securing element 18, 1018 may include a fulcrum 85, 1085 about which the rod 1012 may rotate and the sliding rod support 16, 1016, 1026, 1036 may include a taper 1095, acting as a fulcrum, which contacts a bottom surface 1099 of the rod 1012 or the bottom surface 1050 of the slot 1044. The sliding rod support 16, 1016 may include a first surface 1096 and a second surface 1097. The first surface 1096 of the sliding rod support 1016 may include the taper 1095. When the taper 1095 contacts the bottom surface 1099 (FIG. 3) of the rod 1012, the second surface 1097 of the rod 1012 may have a greater contact area with the bottom surface 1050 of the slot 1044 than when the taper 1095 contacts the bottom surface 1044 of the slot 1050. When the sliding rod support 16, 1016, 1026, 1036 rotates, the center of the sliding rod support 16, 1016, 1026, 1036 serves as an axis of rotation about which the sliding rod support 16, 1016, 1026, 1036 rotates.

The distance of the center 1095 of the sliding rod support 1016, 1026, 1036 from the longitudinal axis 26, 1026 of the bone screw 1000 as the rod 1012 pivots about the fulcrum 1085 of the rod-securing element 1018 may determine the amount of rotation θ of the rod 1012. For example, when the sliding rod support 1016, 1026, 1036 is aligned with the longitudinal axis 1026 of the bone screw 1000 (FIG. 2), the bone screw 1000 does not substantially rotate about the fulcrum 1085 of the rod-securing element 1018, i.e. the axis 1089 of the rod 1012 is substantially perpendicular to the longitudinal axis 1026 of the bone screw 1000. When the center portion of the sliding rod support 1016, 1026, 1036 has traversed a horizontal distance along the bottom surface 1050 of the slot 1044 and is no longer aligned with the longitudinal axis 1026 of the bone screw 1000 (FIGS. 3-5), the rod 1012 rotates about the fulcrum 1085 of the rod-securing element 1018 such that the axis 1089 of the rod 1012 is at an acute angle to the longitudinal axis 1026 of the bone screw 1000.

The amount of rotation of the rod 1012 also depends on the height of the sliding rod support 1016, 1026, 1036 relative to the bottom surface 1050 of the slot 1044. The greater the height of the sliding rod support 1016, 1026, 1036 relative to the bottom surface 1050 of the slot 1044 the less the rod 1012 rotates. The angle of rotation θ may range from substantially 0° to substantially 20° where the maximum angle of rotation θ ranges from substantially 12° to substantially 20°. Preferably, the maximum angle of rotation θ is substantially 15°.

Referring to FIG. 6, which shows a more detailed view of the sliding rod support 1036 within the slot 1044 of FIG. 5, the interior sidewalls 46, 48 of the slot 44 include one or more guide features, shown as projections 54. The projections 54 are configured to be received within corresponding coupling features, i.e. guide channels, of the sliding rod support 16 in order to help guide or facilitate the movement of the sliding rod support relative to the main body 14, as will be discussed in more detail below. The projections 54 are shown generally opposite one another, extending inward from the first interior sidewall 46 and the second interior sidewall 48 of the screw head 24, respectively.

Referring to FIGS. 6-9, the interior sidewalls 46, 48 defining the slot 44 further include a plurality of threads (not shown) at a portion proximate to the top side 40 of the head 24. The threads are configured to mate with the threads (not shown) of the rod-securing element 18 to secure the rod-securing element 18 to the main body 14.

Referring to FIGS. 8 and 10-12, the sliding rod support 16 includes a body 56 having an upper portion 58 generally above a lower portion 60. The sliding rod support 16 is configured to be coupled and movable relative to the main body 14 to provide for adjustment of the cranial or caudal angulation of the longitudinal rod axis 20 relative to the longitudinal screw axis 26 of the bone screw 10.

Figure 11:
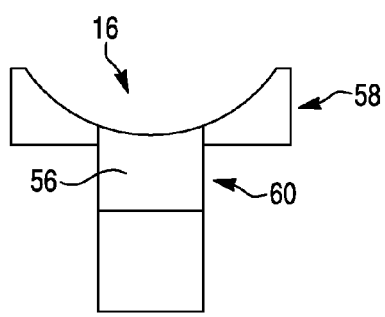
FIG. 11 is a front plan view of the rocker of FIG. 10

Referring in particular to FIGS. 10-11, the upper portion 58 of the sliding rod support 16 includes a surface 62 that is configured to interface with and at least partially support the rod 12. The rod 12 may be disposed on the surface 62, which is shown shaped and sized to generally correspond to the shape and size of the rod. When disposed on the surface 62, the rod 12 is supported a distance above the bottom surface 50 of the slot 44. The rod 12 may also be slidably moved along the surface 62 (e.g., in a direction substantially corresponding to the direction of the longitudinal rod axis 20 to adjust the portion of the rod 12 received within the bone screw 10 before being secured the rod 12 in a desired position).

Figure 12:
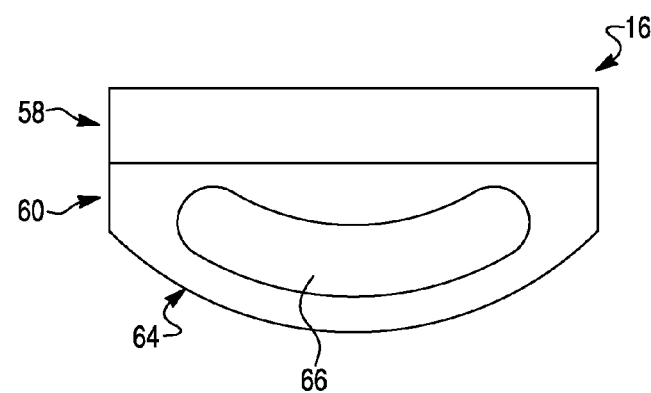
FIG. 12 is a side plan view of the rocker of FIG. 10.

Referring in particular to FIGS. 10 and 12, the lower portion 60 is configured to at least partially interface with the bottom surface 50 of the slot 44 to facilitate movement of the sliding rod support 16 relative to the main body 14. The lower portion 60 includes a curved portion shown as a convex surface 64. The convex surface 64 is shown shaped to generally correspond to the shape of the concave portion 52 of the bottom surface 50 of the slot 44. When the convex surface 64 of the sliding rod support 16 is disposed in contact with the concave portion 52 of the bottom surface 50, the sliding rod support 16 is able to rotate relative to the main body 14 with less resistance (e.g., from friction). Accordingly, the interaction of the surfaces facilitates rotational (e.g., pivotal) movement of the sliding rod support 16 relative to the main body 14.

The concave portion 52 of the bottom surface 50 and the convex surface 64 of the sliding rod support 16 are both shown substantially elongated from front-to-back. This elongation facilitates translational movement of the sliding rod support 16 relative to the main body 14, allowing the sliding rod support 16 to function in a sled or cradle-like manner. This configuration also allows relatively large portions of the surface to remain in contact after an adjustment of the position of the sliding rod support 16 relative to the main body 14. This may be particularly beneficial once the rod 12 is secured relative to the bone screw 10 because the friction between the concave portion 52 and the convex surface 64 can help maintain the rod 12 in a desired position relative to the bone screw 10.

Referring further to FIGS. 10 and 12, the guide features of the sliding rod support 16 are shown as guide channels 66. The guide channels 66 are configured to cooperate with the projections 54 to guide the movement of the sliding rod support 16 relative to the main body 14 in a desired path. The guide channels 66 (e.g., guide cavities, apertures, holes, etc.) shown are formed in a first side 68 and a second side 69 of the sliding rod support 16. The projections 54 are configured to be received in the guide channels 66. When the sliding rod support 16 is moved relative to the main body 14, the interaction of the projections 54 with the guide channels 66 of the sliding rod support 16 causes the sliding rod support 16 to move in a desired path. This path is in a plane 72 corresponding to or substantially parallel to the plane in which the rod 12 is adjustable.

Alternatively, the sliding rod support 16 could include a groove instead of the open channel 66. The projections 54 could be a single pin extending into the open channel 66, or could be studs that extend from both interior side walls 46, 48 and sit in the grooves 66 on each side of the sliding rod support 16. The projections 54 could be friction fit pins or studs, screws, or a combination of both.

Alternatively, other features or structures that help guide the movement of the sliding rod support relative to the main body may be used. These features and structures may be included or integrated with the head, may be included or integrated with the sliding rod support or both. It should also be noted that the interaction of the projections and the guide channels also helps retain the sliding rod support at least partially within the head of the bone screw.

The projection may extend through the walls of the main body. Referring to FIGS. 16A-16D, a bone screw 1410 is shown including a screw head 1424 and a rocker 1416. The rocker is a sliding rod support. The bone screw 1410 is further shown including channels 25 extending from the interior side walls 1446, 1448 of the screw head 1424 to a first exterior side wall 1495 and a second exterior sidewall 1496 of the screw head 1424 to help guide movement of the sliding rod support 1416. It may be easier to manufacture the channels 25 when the channels 25 extend from the interior side walls 1446, 1448 to the first exterior side wall 1495 and the second exterior sidewall 1496 of the screw head 1424 then when the channels 25 do not extend to the first exterior side wall 1495 and the second exterior sidewall 1496 of the screw head. Bone screw 1410 is configured to function in substantially the same manner as bone screw 10.

Figure 13:
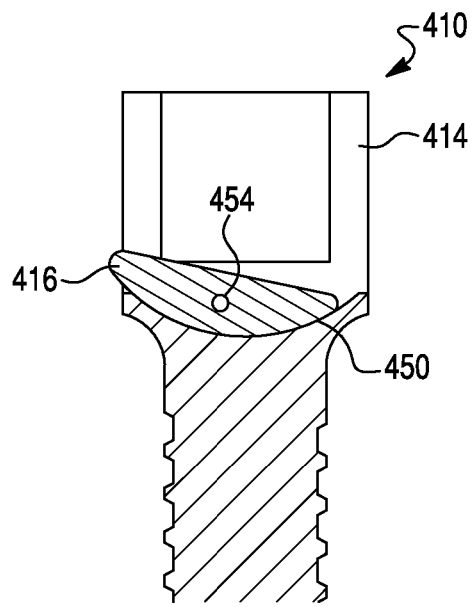
FIG. 13 is a cross-sectional view of a low-profile, uniplanar bone screw with a rod-securing element removed and the rocker having a substantially curved base matching the substantially concave base of the slot.
Figure 14:
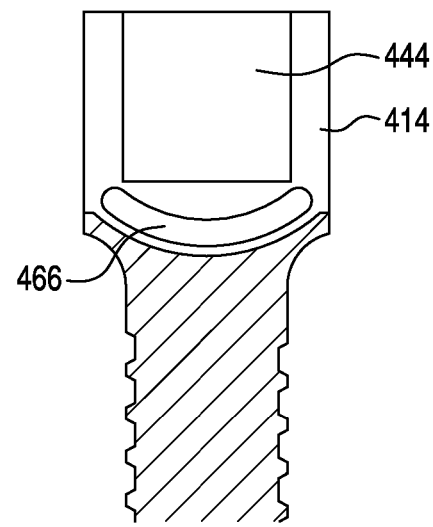
FIG. 14 is a cross-sectional view of the main body of the bone screw of FIG. 13.
Figure 15:
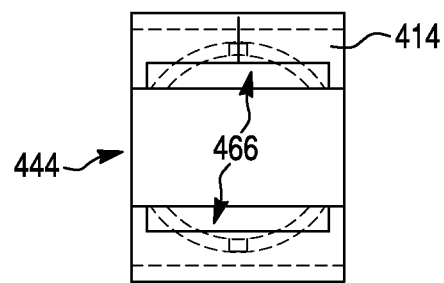
FIG. 15 is a top plan view of the main body of the bone screw of FIG. 13.

The position of the guide features may be switched. Referring to FIGS. 13-15, a bone screw 410 is shown including a main body 414 and a rocker 416. The rocker 416 is a sliding rod support. The bone screw 410 is further shown including guide features, shown as projections 454, and guide channels 466. Rather than the main body including the projections and the sliding rod support including the guide channels as shown in FIGS. 1-4 and 10-12, the sliding rod support 416 is shown including the projections 454 and the main body 414 is shown including the guide channels 466. Generally, the slot includes the guide channels 466. Bone screw 410 is configured to function in substantially the same manner as bone screw 10.

Figure 16A:
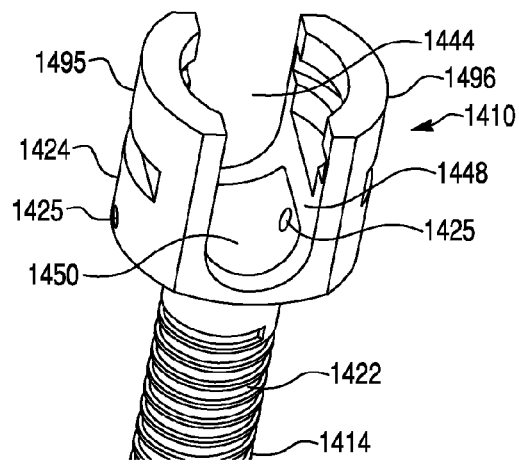
FIG. 16A is a side perspective view of a low-profile, uniplanar bone screw with the rod-securing element and the rocker removed.
Figure 16B:
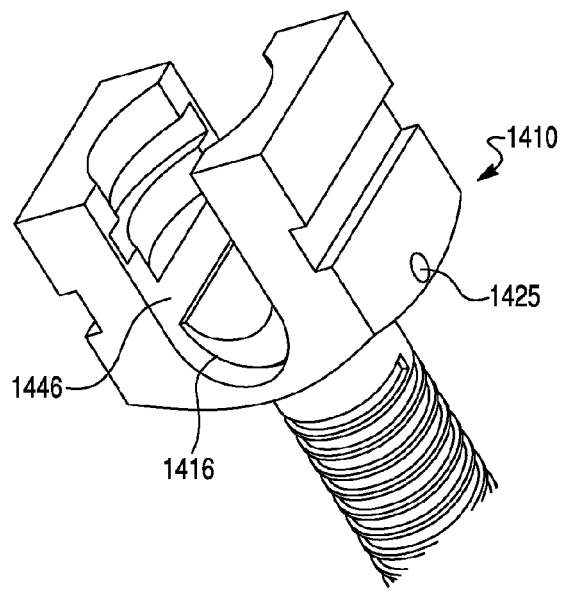
FIG. 16B is a side perspective view of the low-profile, uniplanar bone screw of FIG. 16A.
Figure 16C:
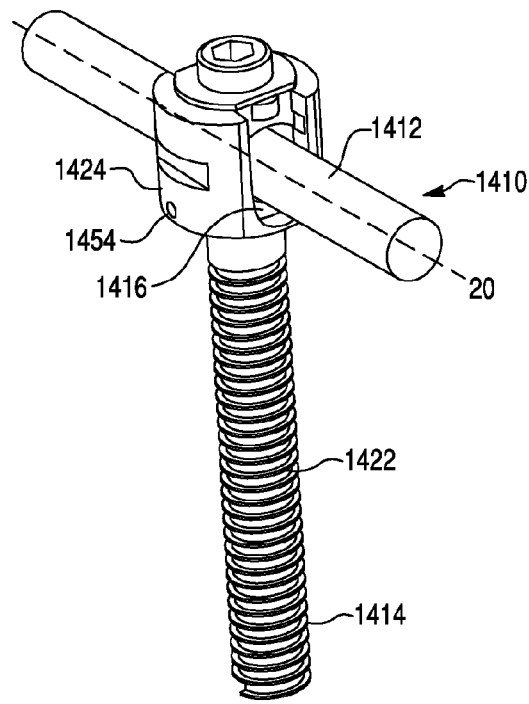
FIG. 16C is a side perspective view of the low-profile, uniplanar bone screw of FIG. 16A with a rod-securing element, rocker and rod.
Figure 16D:
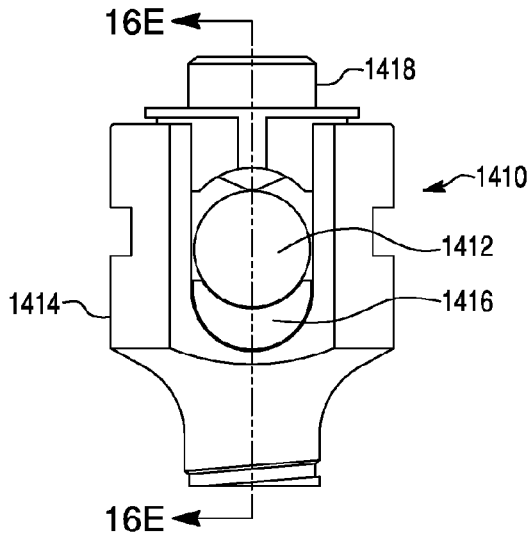
FIG. 16D is a front plan view of the screw head of the low-profile, uniplanar bone screw of FIG. 16C.
Figure 16E:
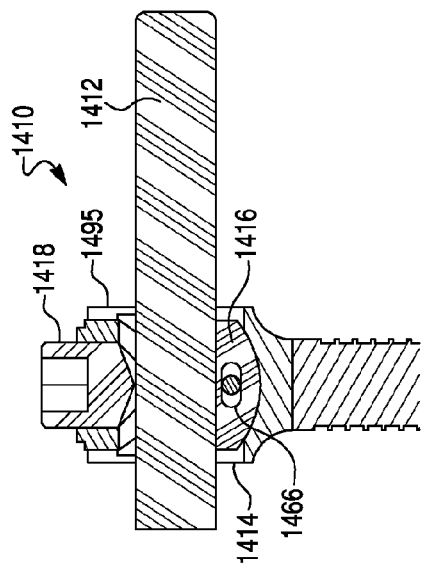
FIG. 16E is a cross-sectional view of the low-profile, uniplanar bone screw of FIG. 16D taken along line 16E-16E.
Figure 16H:
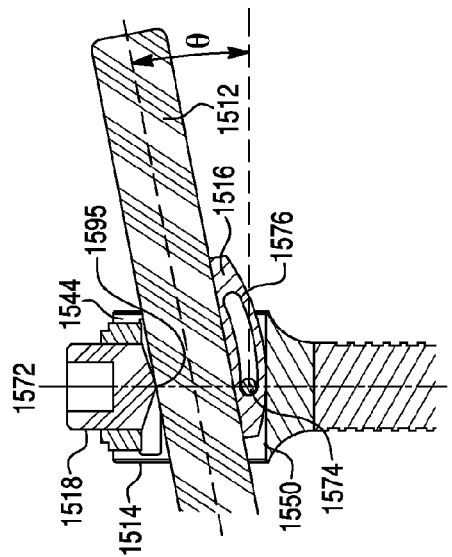
FIG. 16H is a cross-sectional view of a low-profile, uniplanar bone screw with a substantially flat slot base and with a rod rotated relative to the fulcrum of the rod-securing element.
Figure 16G:
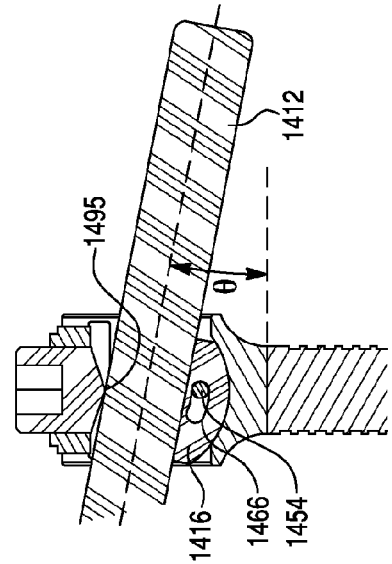
FIG. 16G is a cross-sectional view of a low-profile, uniplanar bone screw with a rod rotated relative to the fulcrum of the rod-securing element.
Figure 16F:
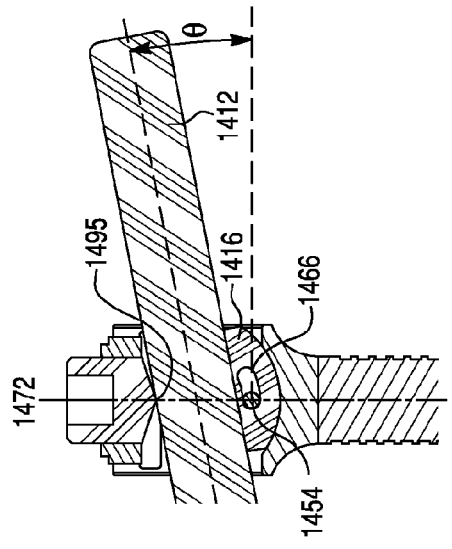
FIG. 16F is a cross-sectional view of the low-profile, uniplanar bone screw of FIG. 16D with a rod rotated relative to the fulcrum of the rod-securing element.

Referring to FIGS. 16E-16H, the width of the guide channels 1466 of the sliding rod support 1416 may vary. As shown in FIGS. 16E-16G, the width of the guide channels 1466 may be narrower than the guide channels 66 of FIGS. 8, 10 and 12, thereby allowing the width of the screw head 1414 to be smaller than the width of the screw head 14 of FIGS. 6-9. Alternatively, as shown in FIG. 16H, the width of the guide channel 1576 may be wider than the guide channel of FIGS. 1-4. The width of the guide channel 1576 may range from substantially 3 mm to substantially 12 mm and is preferably substantially between 5-6 mm. The wider the width of the guide channels relative to the width of the projection, the greater the maximum degree of rotation for the rod can be. Both bone screws 1410 and 1510 are configured to function in substantially the same manner as bone screw 10. The height of the guide channels may range from 0.5 mm to 1.2 mm. A concave surface of the slot (FIGS. 16E-16G) allows for a larger height of the guide channels than a flat surface of the slot (FIG. 16H).

The fulcrum of the rod-securing element may be pointed or curved. As shown in FIGS. 16E-16H, the fulcrum 1495, 1595 of the rod-securing element 1418, 1518 may be pointed. As shown in FIGS. 17A-17C, the fulcrum 1695 of the rod-securing element 1618 may be curved. In contrast to the pointed fulcrum, the curved fulcrum helps prevent the fulcrum 1695 of the rod-securing element 1618 from damaging the rod but allows for a smaller maximum degree of rotation of the rod. Bone screw 1610 is configured to function in substantially the same manner as bone screw 10.

Referring back to FIGS. 6-9, when the rod 12 is supported on the sliding rod support 16, the sliding rod support 16 guides the motion of the rod 12 as it is adjusted. As noted above, the motion of the sliding rod support 16 is in a plane corresponding to or substantially parallel to the plane in which the rod is adjustable. As the angle of the rod 12 is adjusted with the plane 72, the sliding rod support 16 guides the motion of the rod 12 and provides support for the rod 12 relative to the main body 14 of the bone screw 10. Adjusting the rod 12, changes the angle of the longitudinal rod axis 20 relative to the longitudinal screw axis 26 (see, e.g., FIG. 8). For the purposes of discussion, the neutral position of the rod 12 relative to the bone screw 10 is one wherein the longitudinal rod axis 20 is substantially perpendicular to the longitudinal screw axis 26. The rod 12 may be adjusted within the plane 72 to approximately +/−16 degrees from the neutral position. The structure of the bone screw may be changed to provide for greater adjustability (e.g., approximately +/−20 degrees) or to limit the adjustability of the rod (e.g., approximately +/−7 degrees). The rods 1412, 1512, 1612 of FIGS. 16F-16H and 17C may also be adjusted within planes 1472, 1572 and 1672 a similar amount to that of rod 12.

Referring further to FIGS. 4-9 and 16H, the motion of the sliding rod support 16, 1016, 1516 as it is moved in the path defined by the guide channels 66 includes a translational component of motion. Accordingly, the movement of the rod 12, 1012 as it is adjusted typically may includes localized rotation in addition to a translational component of motion of the sliding rod support 16, 1016, 1516.

Referring further to FIGS. 6-9, rod-securing element 18 is configured to secure the rod 12 in the desired position relative to the bone screw 10.

The rod-securing element 18 includes threads that are configured to mate with the threads, as mentioned above. Positioning a portion of the rod-securing element 18 into the slot 44 and rotating the rod-securing element 18 about an axis substantially corresponding to the longitudinal screw axis 26, threadably engages the rod-securing element 18 with the head 24.

The rod-securing element 18 further includes an upper portion 74 and a lower portion 76. Referring to FIG. 8, the upper portion 74 includes an engagement feature 78. The engagement feature 78 is configured to be engaged by a tool to facilitate rotation, and thereby, securing, of the rod-securing element 18 to the main body 14. Referring to FIGS. 6 and 3, the lower portion 76 is configured to contact the rod 12 and, thereby, to apply a force to the rod 12 that helps maintain the rod 12 in the desired position. This contact point to the rod defines the fulcrum about which the rod rotates in the plane of the screw-head slot.

Further referring to FIG. 8, the lower portion 76 of the rod-securing element 18 is preferably configured to be generally pointed. A surface 80 defining the pointed lower portion 76 of the rod-securing element 18 is angled, providing for improved contact between the rod-securing element 18 and the rod 12 to help hold the rod 12 in position. It should be noted that the translational movement of the rod 12 provided by the sliding rod support 16, helps the rod 12 to be brought into improved contact with the surface 80 of the rod-securing element 18. Without this translational component of motion, the sliding rod support and the rod have the tendency to move toward the neutral position when used with rod-securing element 18.

The position of the rocker and the pointed lower portion may be switched. Referring to FIGS. 18-21B, a bone screw 510 includes a main body 514, a rocker 516, 1516, a rod-securing element 580, a set screw 518 and a connector 586. Referring to FIG. 18, the main body 514 is shown including a slot 544 and threads 572. The slot 544 is shown including a bottom surface 550 that has a pointed portion 576, similar to the pointed, lower portion 76 of rod-securing element 18. A surface 580 defining the pointed portion 576 is angled, providing for improved contact with a rod when a rod is disposed within slot the 544 and coupled to the bone screw 510. The surface 580 is a rod-securing element. The pointed portion 576 of the rod-securing element 580 serves as a fulcrum and the fulcrum serves as an axis of rotation about which the rod rotates. The threads 572 are configured to receive the set screw 518.

Figure 21A:
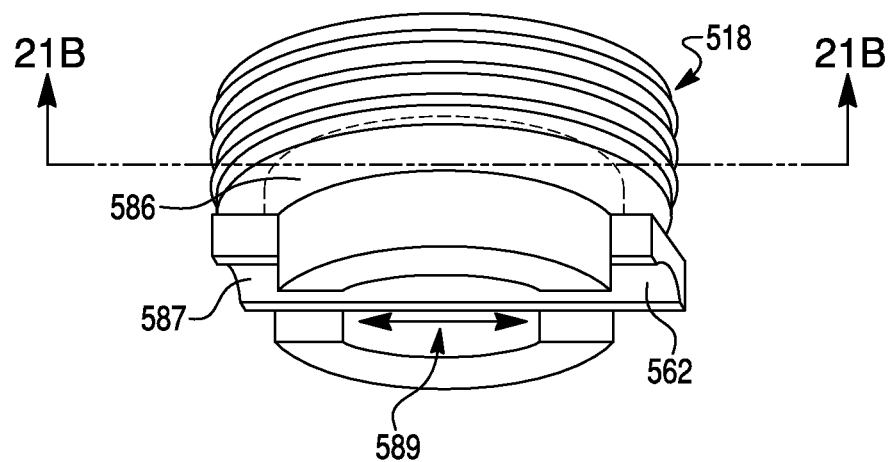
FIG. 21A is a side view of the rocker, set screw and connector of the low-profile, uniplanar bone screw of FIG. 18.

The rocker 516, 1516 is a sliding rod support. As shown in FIGS. 19 and 21A, the rocker 516 includes a sliding plate support 571 that allows for rotational movement of the rocker 516 where the rocker 516 rotates about the sliding plate support 571. The sliding rod support 516 may fit within a first or cylindrical portion 586. The first or cylindrical portion 586 is a connector. The surface of the first or cylindrical portion 586 is substantially smooth. A second portion 587 of the sliding rod support 516 is retained within a slot 589 of the connector 586 by a projection 590 that also serves as a pivot point. The projection 590 (e.g., pin) may be received in any suitable corresponding guide or retention feature (e.g., a groove or a channel). The ends 592 of the projection 590 may or may not be flush with the outer surface 591 of the slot 589. When the ends 592 of the projection 590 are not flush with the outer surface 591, the rocker 516 is able to translate with respect to the connector 586. A surface 562 of the sliding rod support 516 is shown facing generally downward, to contact and help guide a rod received in the bone screw 510 and the surface 562 of the sliding rod support 516.

The sliding rod support may include a flat or curved surface that abuts the connector. FIG. 19 illustrates a sliding rod support 516 that includes a flat surface 595 that abuts the connector 586. FIG. 20B illustrates a sliding rod support 1516 with a curved surface 596 that would abut the connector 586. Like the sliding rod support 516, the sliding rod support 1516 also includes a projection 1590.

Figure 21B:
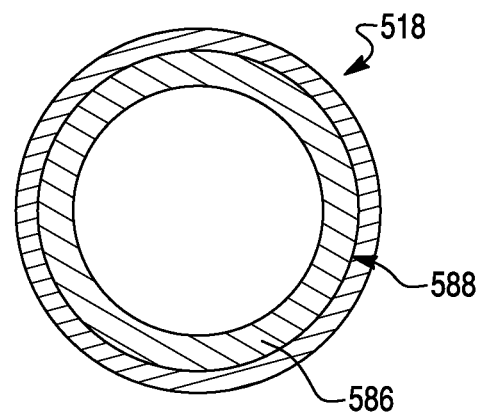
FIG. 21B is a cross-sectional view of the set screw and the connector of FIG. 21A taken along line 21B-21B.
Figure 22:
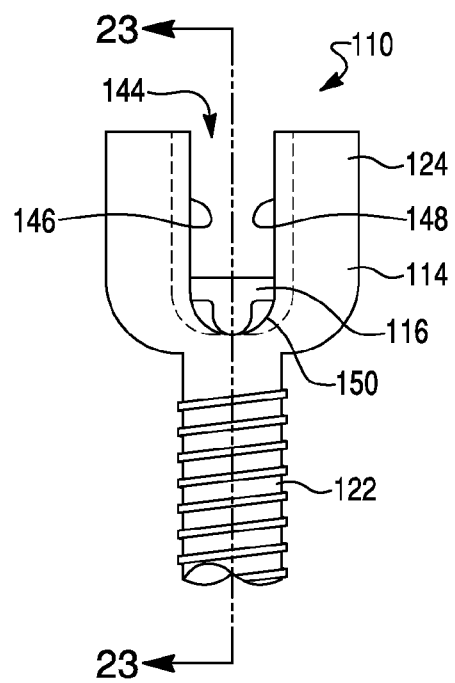
FIG. 22 is a front view of a low-profile, uniplanar bone screw.
Figure 23:
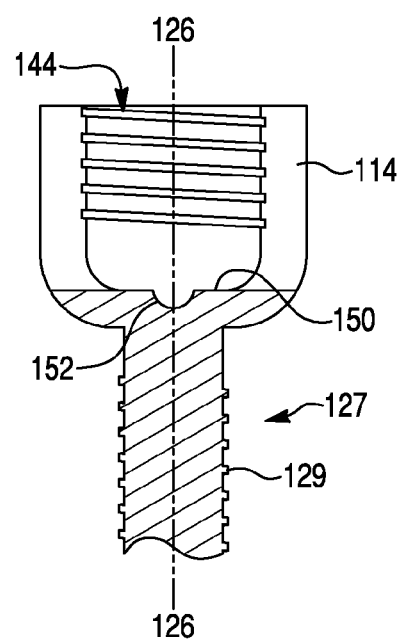
FIG. 23 is a cross-sectional view of the low-profile, uniplanar bone screw of FIG. 22 taken along line 23-23 with the rocker removed.
Figure 24:
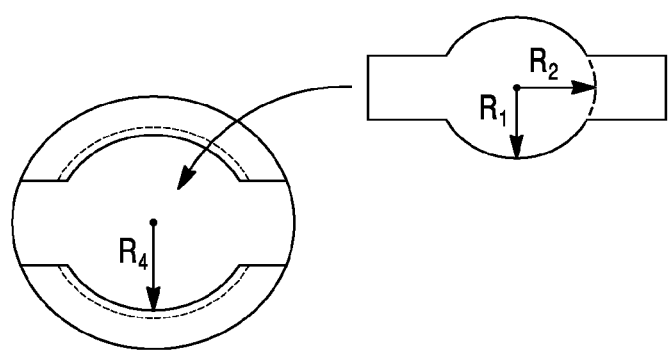
FIG. 24 is a top plan view of the rocker of the low-profile, uniplanar bone screw of FIG. 22.
Figure 25:
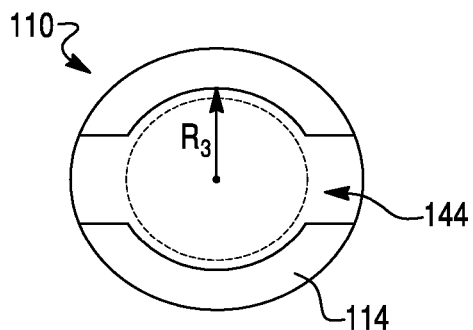
FIG. 25 is a top plan view of a main body of the low-profile, uniplanar bone screw of FIG. 22.
Figure 26:
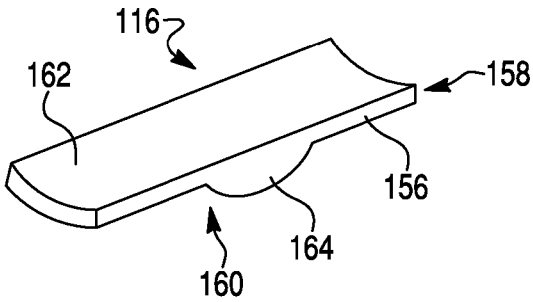
FIG. 26 is a perspective view of the rocker of the low-profile, uniplanar bone screw of FIG. 22.
Figure 27:
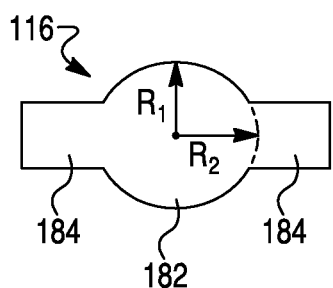
FIG. 27 is a top plan view of the rocker of FIG. 26.
Figure 28:
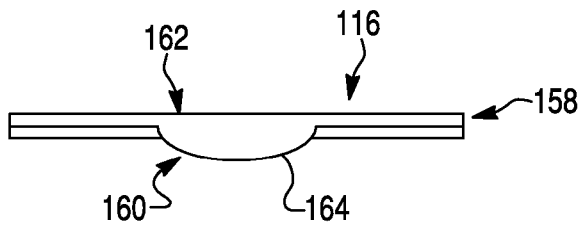
FIG. 28 is a side plan view of the rocker of FIG. 26.
Figure 29:
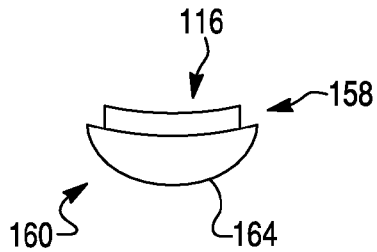
FIG. 29 is a front end plan view of the rocker of FIG. 26.
Figure 30:
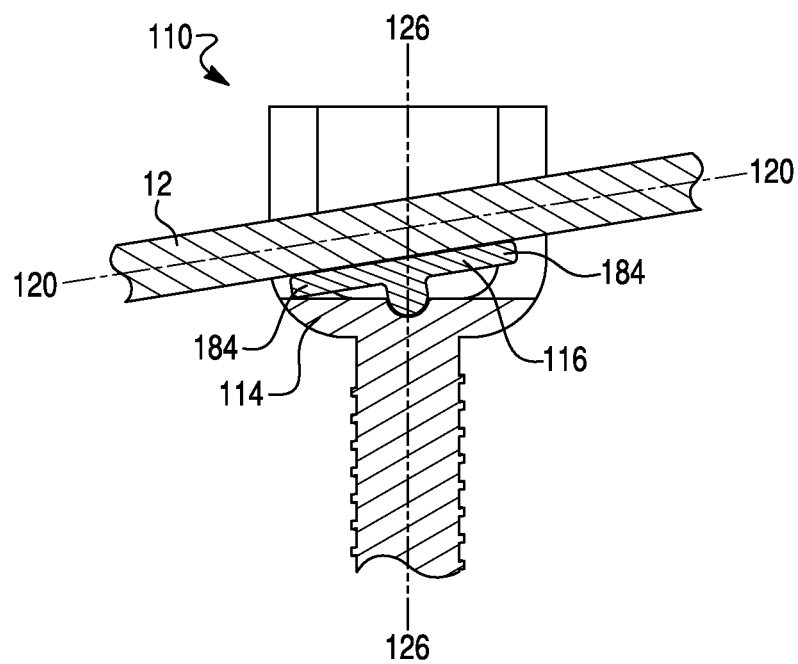
FIG. 30 is a cross-sectional view of the low-profile, uniplanar bone screw of FIG. 22 with a rocker and rod disposed in a slot and a rod-securing element removed.
Figure 31:
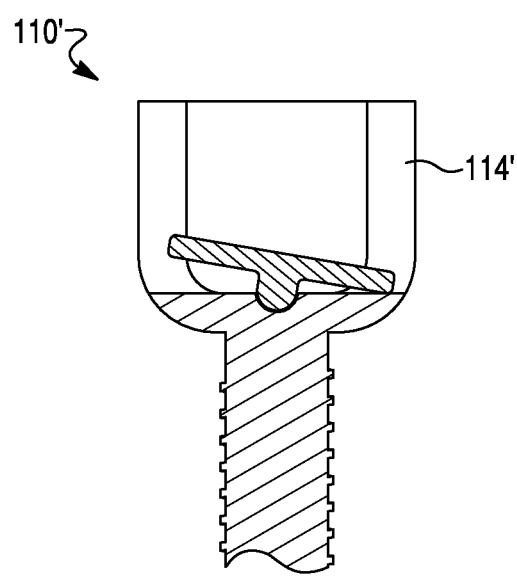
FIG. 31 is an alternative cross-sectional view of the low-profile, uniplanar bone screw of FIG. 22 with a rocker disposed in a slot and the rod and rod-securing element removed.

As shown in FIG. 21B, the set screw 518 is configured to receive the connector 586. The connector 586 may be received within a groove 588 of the set-screw 518. The interaction between the connector 586 and groove 588 provides for the surface 562 of the sliding rod support 516 to remain substantially parallel to a rod received in the slot 544 of the bone screw 510 when the rod-securing element 580 is coupled to or integrated with the main body 514.

This "inverted embodiment" functions in substantially the same manner as bone screw 10, described above. The motion of the sliding rod support 516 may include a rotational component of motion and a translational component of motion. Accordingly, the movement of a rod that is coupled to the bone screw 510 as it is adjusted typically includes both a rotational and a translational component of motion.

Referring to FIGS. 22-31, a bone screw 110 including a main body 114 and a rocker 116 is shown.

Similar to main body 14, the main body 114 includes a shaft 122 and a head 124. The shaft 122 includes a threaded portion 127 including a plurality of threads 129. The head 124 includes a slot 144 having a first interior sidewall 146 generally opposite a second interior sidewall 148 and a bottom surface 150. The sidewalls 146, 148 are shaped to accommodate the rocker 116 and help retain the rocker 116 within the head 124, as will be discussed in more detail below. The bottom surface 150 includes a curved portion 152 in which the rocker may glide but also retains the rocker from displacing outside of the slot or recess for a dome 157 of the rocker 116.

Referring in particular to FIGS. 25-29, the rocker 116 includes a body 156 having an upper portion 158 generally above a lower portion 160. Similar to the sliding rod support 16, the rocker 116 is configured to be coupled and movable relative to the main body 114 to provide for adjustment of the cranial or caudal angulation of a longitudinal rod axis 120 relative to the longitudinal screw axis 126.

Similar to sliding rod support 16, the upper portion 158 of the rocker 116 includes a surface 162 that is configured to at least partially support the rod 12, and the lower portion 160 is configured to at least partially interface with the bottom surface 150 of the slot 144 to facilitate movement of the rocker 116 relative to the main body 114. Also similar to the sliding rod support 16, the lower portion 160 includes a curved portion.

However, unlike the convex surface 64 of the sliding rod support 16, the curved portion is shown as a convex portion 164 that is substantially dome-shaped. The interaction between the concave portion 152 (e.g., recess, etc.) of the bottom surface 150 of the slot 144 and the convex portion 164 of the rocker 116 is configured to provide for substantially rotational movement of the rocker 116 relative to the main body 114. The concave portion 152 of the bottom surface 150 of the slot 144 and the convex portion 164 of the rocker 116 is in contact with concave portion 152 of the bottom surface 150. The dome-shaped convex surface 164 is substantially configured to raise a portion of the rocker 116 a distance above the bottom surface 150 of the slot 144 when in contact therewith. This distance facilitates rod rotation in addition to the rocker 116 gliding back-and-forth within the slot 144 substantially. It should be noted that, the concave portion of the bottom surface may be larger (e.g., larger than shown in FIG. 16) and/or elongated to also provide for translation of the rocker relative to the main body. It should also be noted that the dome may be substantially any at least partially curved projection (e.g., semi-cylinder, etc.).

Further, the rocker 116 does not rely on guide channels and projections to guide it and retain it within the head 124. Rather, the rocker 116 is retained in the head because the slot 144 is shaped to substantially confine the rocker 116. That is, the upper portion 158 of the rocker includes a substantially elliptical portion 182 and wings 184 (i.e. a first wing and a second wing) that are configured to confine the rocker 116 within the screw head 124 of the main body 114. While the wings 184 extend substantially from front-to-back or a first end to a second end of the substantially elliptic portion 182 within the slot 144, the size and shape of the elliptical portion 182 substantially prevents the rocker 116 from falling out of the head 124.

Figure 32:
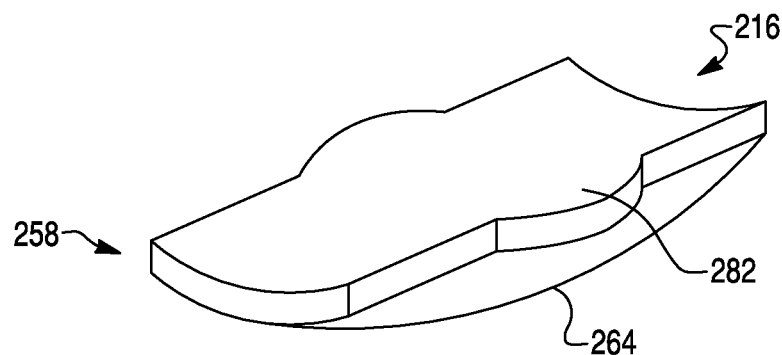
FIG. 32 is a perspective view of a rocker.
Figure 33:
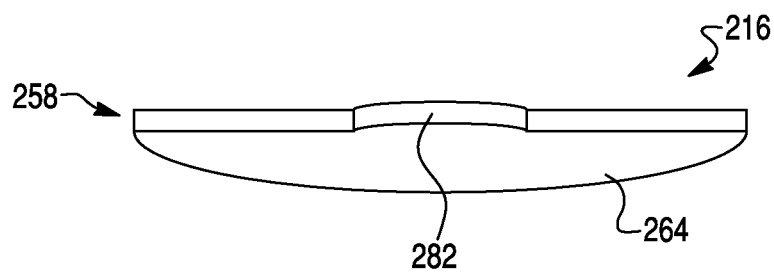
FIG. 33 is a side view of the rocker of FIG. 32.
Figure 34:
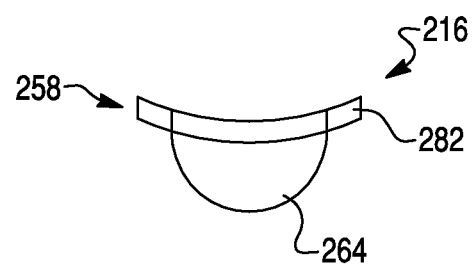
FIG. 34 is a front end view of the rocker shown in FIG. 32.

Referring to FIGS. 32-34, a rocker 216 is shown. The rocker 216 is intended to function similar to rocker 116 in that it is configured to provide for rotational motion in addition to translation of the rocker 216 relative to a main body and is configured to be retained in a head of the main body of a bone screw because of the fit between a substantially elliptical portion 282 of an upper portion 258 and a slot of the head. In contrast to rocker 116, however, the curved portion of rocker 216, shown as convex portion 264, is substantially an elliptical dome rather than a substantially circular dome like convex portion 164. Other curved portions are contemplated. For example, the bottom surface of the bone screw may include a convex portion and the rocker may include a concave portion.

Figure 35:
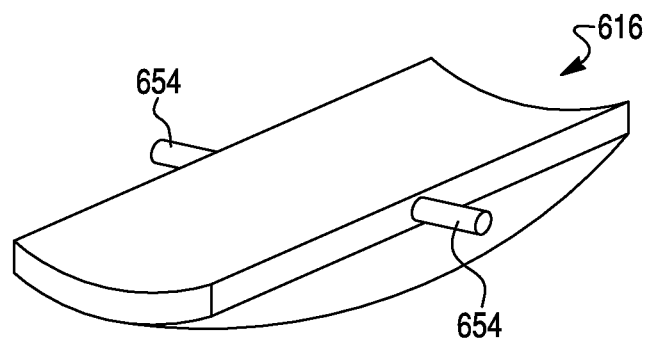
FIG. 35 is a perspective view of a rocker.
Figure 36:
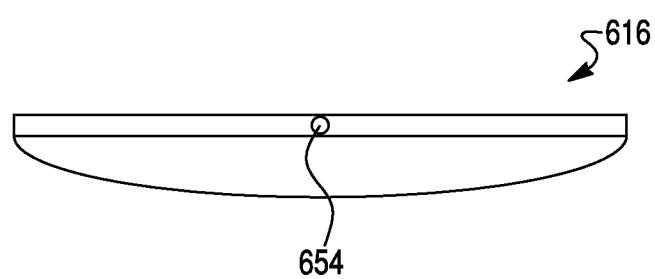
FIG. 36 is a side view of the rocker of FIG. 35.
Figure 37:
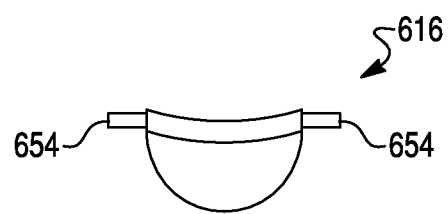
FIG. 37 is a front end view of the rocker shown in FIG. 35.

Referring to FIGS. 35-37, a rocker 616 is shown. The rocker 616 is shown substantially similar to rocker 216 except that it includes a guide feature, shown as projections 654, rather than an elliptical portion to help retain it within a head of a bone screw. The projections 654 are configured to be received within corresponding guide feature (e.g., guide channels) in a bone screw (e.g., similar to bone screw 410, discussed above).

Figure 38:
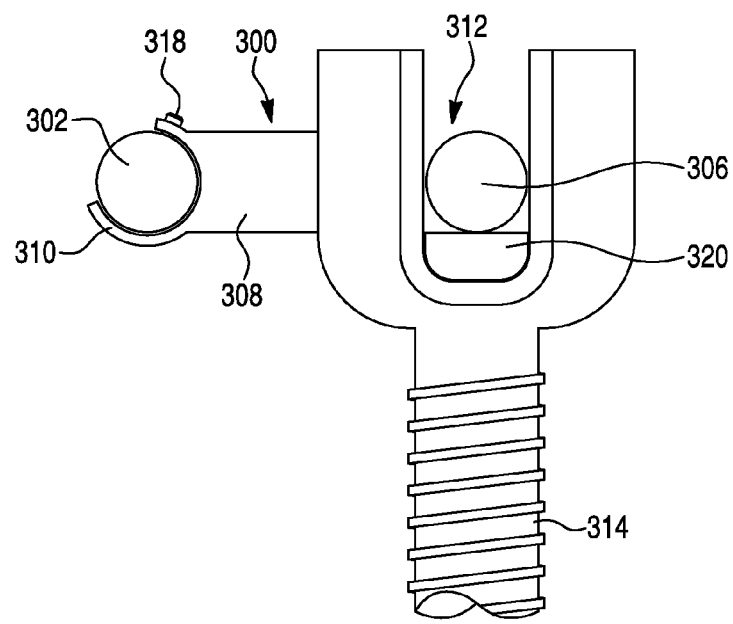
FIG. 38 is a perspective view of an outrigger assembled with a low-profile, uniplanar bone screw.
Figure 39:
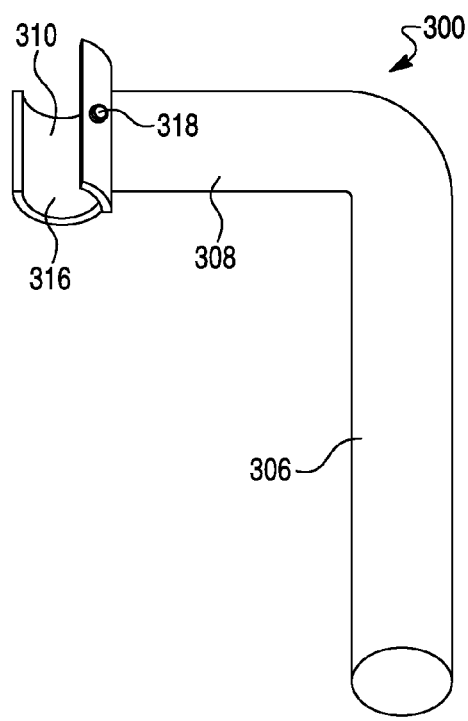
FIG. 39 is a perspective view of the outrigger shown in FIG. 38.
Figure 40:
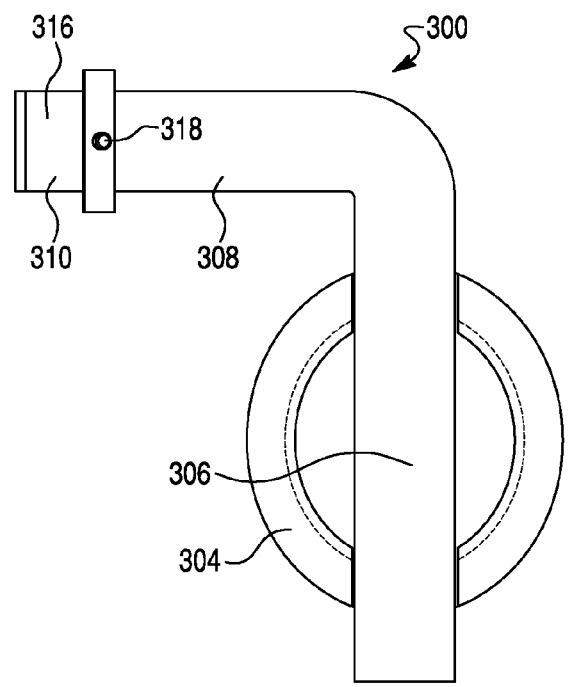
FIG. 40 is a top plan view of the outrigger shown in FIG. 38.

Referring to FIGS. 38-40, an outrigger 300 configured to be utilized with a bone screw is shown. The outrigger 300 is configured to provide for coupling of a rod 302 to a bone screw 304 such that the rod 302 is offset relative to the bone screw 304. The outrigger 300 is shown including a first member 306, a second member 308, and a rod coupling portion 310. The first member 306 and the second member 308 are shown integrally formed such that they are at an angle to one another (shown here as approximately 90 degrees). The rod coupling portion 310 is shown disposed at the end of the second member 308 distal to where the second member 308 and the first member 306 meet or coincide. It should be noted that the first member and the second member may be disposed at an angle relative to each other that is other than 90 degrees (e.g., 75 degrees). It should also be noted that, while the first member, the second member and the rod coupling portion are shown integrally formed, they need not be. For example, the first member and the second member may be integrally formed while the rod coupling portion is secured to an end of the second member (e.g., by screws, an adhesive, etc.).

The first member 306 of the outrigger 300 is configured to be received in a slot 312 of the bone screw 304 and secured to a main body 314 of the bone screw 304 in a manner that is substantially similar to how rod 12 is coupled to the main body 14 of bone screw 10. When the first member 306 of the outrigger 300 is received within the slot 312, the second member 308 extends a distance outward to a side of the bone screw 304.

The rod-coupling portion 310 is shown as a clamp. The rod 302 may be positioned in a hook-shaped portion 316 of the clamp 310 and then secured thereto with a screw 318 before or after the first member 306 of the outrigger 300 is at least partially received in the slot 312. As mentioned above, the rod coupling portion 310 is shown disposed at the end of the second member 308 distal to where the second member 308 and the first member 306 meet or coincide. Thus, when the rod 302 is coupled to the outrigger 300 by the rod coupling portion 310, it is offset a distance from the longitudinal screw axis. Alternatively, the rod-coupling portion may be any combination of elements suitable for securing the rod relative to the first and second members.

The bone screw 304 further includes a rocker 320. The rocker 320 is configured to provide for adjustment of the outrigger 300, and, thus, the rod 302, relative to the bone screw 304 in a plane corresponding to or parallel to the plane generally defined by the slot 312. The rocker may be configured in any suitable manner providing for at least rotational (e.g., pivotal, rocking, etc.) motion of the rod relative to the bone screw, as described in more detail above.

Figure 41:
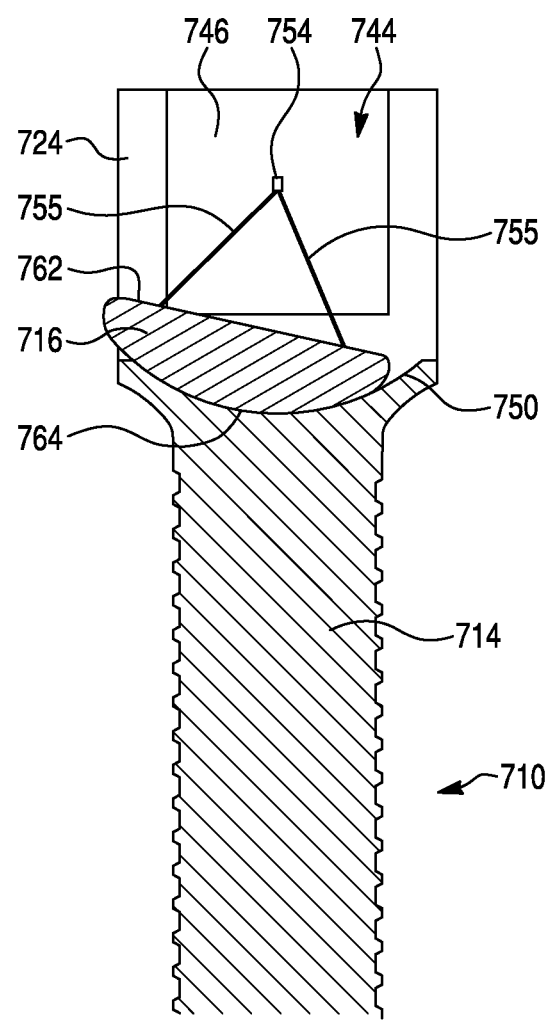
FIG. 41 is a cross sectional view of a low-profile, uniplanar bone screw with a swing.
Figure 42:
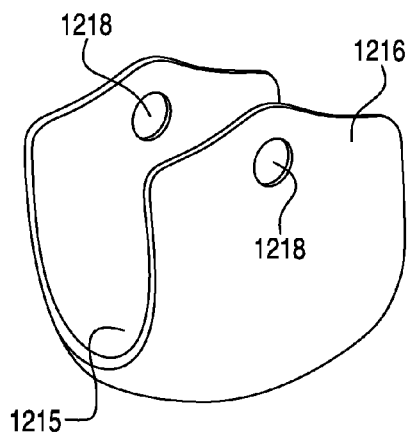
FIG. 42 is a side perspective view of a swing.
Figure 43:
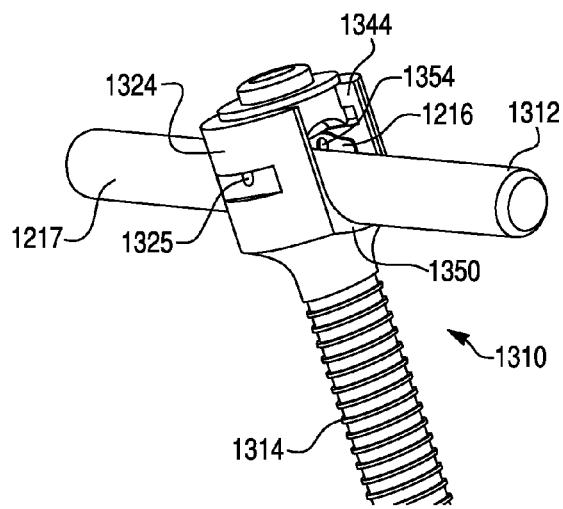
FIG. 43 is a side perspective view of a low-profile uniplanar bone screw with the swing of FIG. 42.
Figure 44:
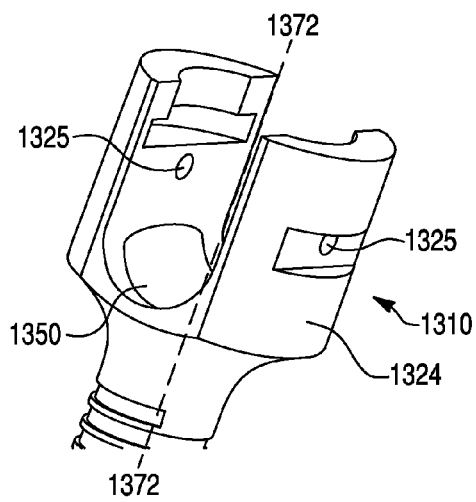
FIG. 44 is a side perspective view of a low-profile uniplanar bone screw with a substantially curved bottom surface of FIG. 43 with the rod-securing element and swing removed.

Referring to FIG. 41, a low-profile bone screw 710 is shown. The bone screw 710 is shown substantially similar to bone screw 410 except that the bone screw 710 includes a projection 754 from which a rocker 716 is suspended. The rocker 716 is a swing or a swing sliding support. The projection (pin, protrusion, etc.) 754 extends out from an interior wall 746 of a head 724 of a main body 714 of the screw 710. One or more suspension lines 755 (two are shown) suspend the swing 716 in the slot 744 of the screw head 724. The suspension lines 755 may be rigid, allowing the swing 716 to pivot about projection 754. Thus, the projection 754 acts as a pivot point or hinge. The suspension lines 755 may be a thin rod or wire, or a triangular plate that is integral with the swing 716. The suspension lines 755 may include a hole (not shown) through which the projection 754 is coupled to the suspension line 755. The projection 754 can be a screw or other suitable fastener that extends from wall 746. Alternatively, an end portion of the suspension line 755 includes the projection 754 and the wall 746 includes a receiving hole for the projection 754.

The swing 716 includes an upper surface 762 on which a rod would contact or interface and a bottom convex surface 764. The bottom convex surface contacts or interfaces with a flat or curved bottom surface 750 of the slot 744. The swing 716 is configured to swing freely without a load or seat firmly against the base or bottom surface 750 of the slot 744 when under a load, such as from a rod. The tolerances at the projection 754 enable the swing 716 to swing freely without the load. In other words, the projection 754 may be smaller than the receiving hole that the projection 754 fits into so that the projection 754 and receiving hole have a loose fit. The rod rotates about the tip of the tapered fixation screw which coincides with the projection or hinge.

As shown in FIGS. 42-44 and 49B-50C, a swing 1216 (FIG. 42) may include holes 1218 for receiving one or more guide features 1254 (e.g. a projection) (FIG. 43) that is configured to couple the swing 1216 to the screw head 1324 of the main body 1314 of the bone screw 1310. The holes 1218 also serve as an axis of rotation about which the swing 1216 rotates. The screw head 1324 includes holes 1325 for receiving one or more projections 1354. The projections 1354 are configured to couple the swing 1216 to the bone screw 1310 such that the swing 1216 can rotate about a fulcrum 1385 of a rod securing element 1380 relative to the screw head 1324 of the bone screw 1310. For example, as shown in FIGS. 49A, 49C, 50A and 50C, the swing 1216 may rotate about the fulcrum 1385 from a first position (FIGS. 49A, 49C) where the longitudinal axis 1220 of the rod 1212 is substantially perpendicular to the longitudinal axis 1370 of the bone screw 1310 to a second position (FIGS. 50A, 50C) where the longitudinal axis 1220 of the rod 1212 is at an angle to the longitudinal axis 1370 of the bone screw 1310. When the swing 1216 is coupled to the bone screw 1310, a bottom surface 1217 of the rod 1312 abuts a surface 1215 of the swing 1216 and the swing 1216 abuts a bottom surface 1350 of the slot 1344.

Figure 46A:
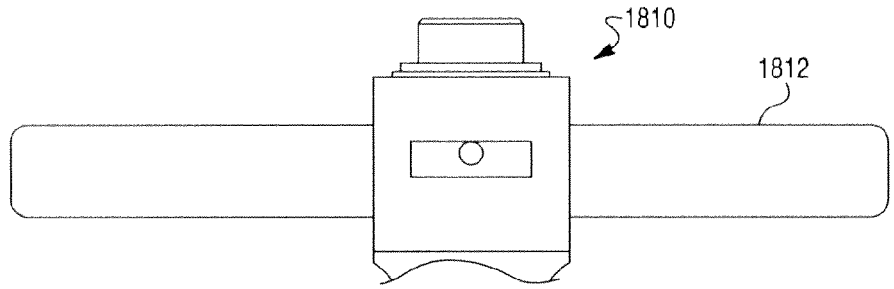
FIG. 46A is a side plan view of a low-profile uniplanar bone screw.
Figure 46B:
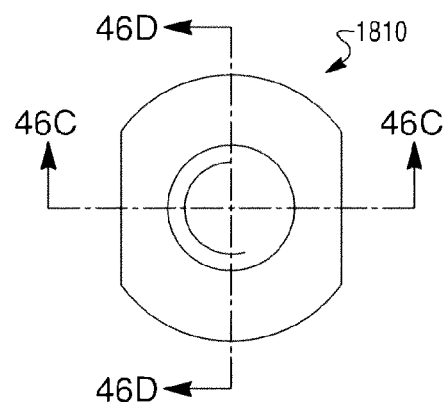
FIG. 46B is a top view of the low-profile, uniplanar bone screw of FIG. 46A.
Figure 46C:
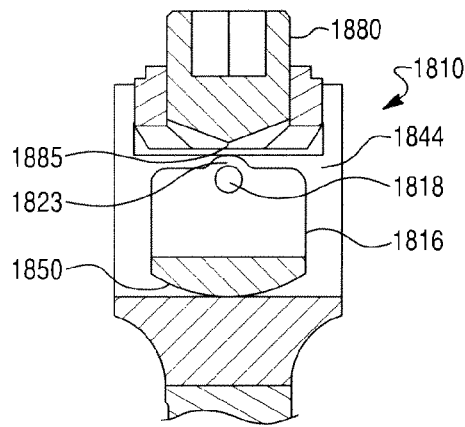
FIG. 46C is a cross-sectional view of the low-profile, uniplanar bone screw of FIG. 46B taken along line 46C-46C.
Figure 46D:
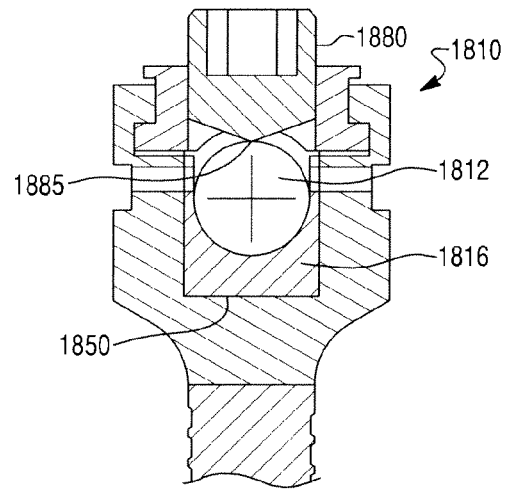
FIG. 46D is a cross-sectional view of the low-profile, uniplanar bone screw of FIG. 46B taken along line 46D-46D.

The screw head 1324 includes a bottom surface 1350. The bottom surface 1350 of the slot 1344 of the bone screw 1310 may be substantially curved in a first direction (FIGS. 49C and 50C) and substantially curved in a second direction (FIGS. 49D and 50D) where the second direction is substantially transverse to the first direction. The curved surfaces of the bottom surface 1350 allow a lower profile of the bone screw and a larger maximum degree of rotation of the swing 1216 than when the bottom surface is substantially flat in any direction (FIG. 46C). Bone screw 1310 is configured to function substantially the same way as bone screw 10.

Figure 45:
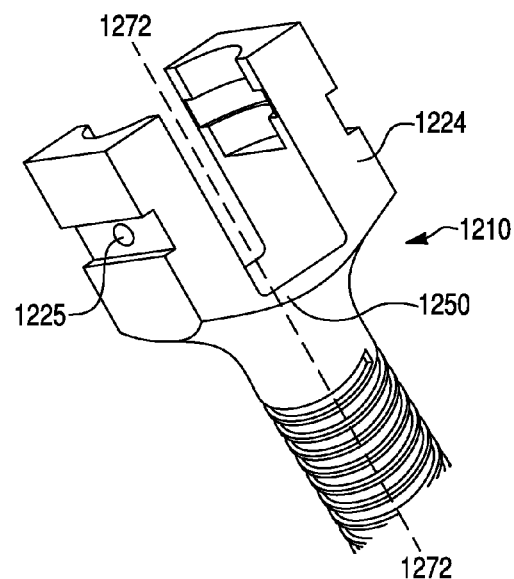
FIG. 45 is a side perspective view of the low-profile, uniplanar bone screw with a substantially flat bottom surface.

The bottom surface of the bone screw may not be curved. As shown in FIG. 45, the bottom surface 1250 of the bone screw 1210 may be substantially flat in a first direction and substantially flat in a second direction that is substantially transverse to the first direction. The substantially flat bottom surface 1250 in the first and second direction leads to a decreased range of rotational motion of the swing 1216 relative to the fulcrum of the rod-securing element as compared to the range of rotational motion when the bottom surface is substantially curved in a first and second direction. Bone screw 1210 is configured to function substantially the same way as bone screws 10.

The bottom surface of the bone screw may be curved in one direction and flat in another direction. As shown in FIGS. 46A-48D, the bottom surface 1850, 1950 of the bone screw 1810, 1910 may be substantially curved in a first direction (FIGS. 46C, 47C, 48C) and substantially flat in a second direction (FIGS. 46D, 47D, 48D) that is substantially transverse to the first direction. Bone screws 1810, 1910 are configured to function substantially the same way as bone screw 10.

Figure 47A:
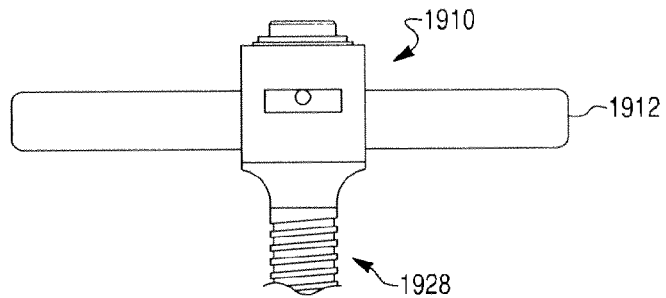
FIG. 47A is a side plan view of a low-profile, uniplanar bone screw.
Figure 47B:
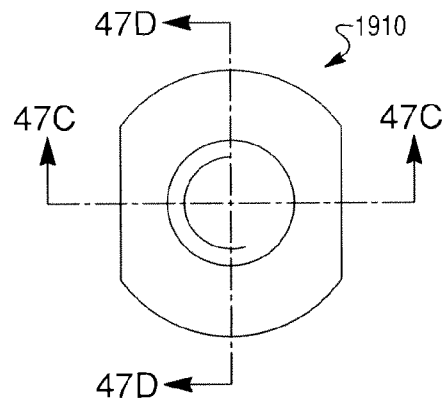
FIG. 47B is a top view of the low-profile, uniplanar bone screw of FIG. 47A.
Figure 47C:
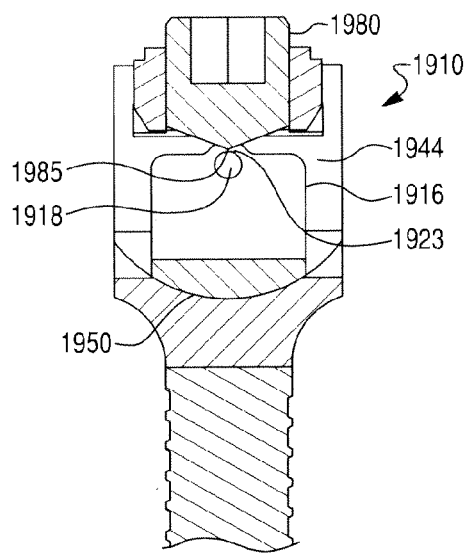
FIG. 47C is a cross-sectional view of the low-profile, uniplanar bone screw of FIG. 47B taken along line 47C-47C.
Figure 47D:
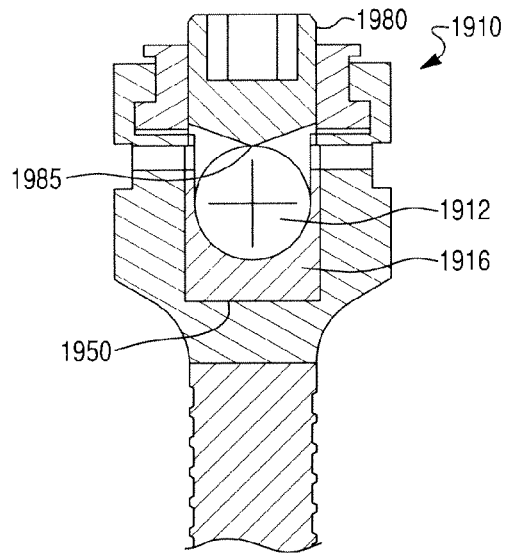
FIG. 47D is a cross-sectional view of the low-profile, uniplanar bone screw of FIG. 47B taken along line 47D-47D.
Figure 48A:
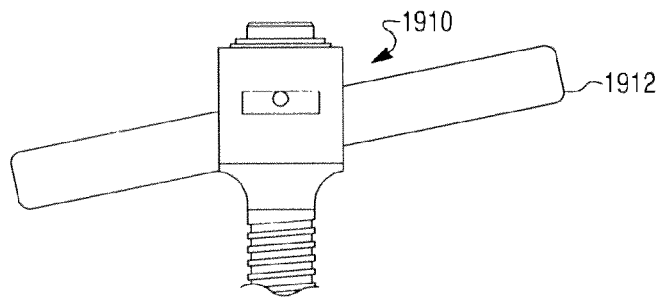
FIG. 48A is a side plan view of a low-profile, uniplanar bone screw.
Figure 48B:
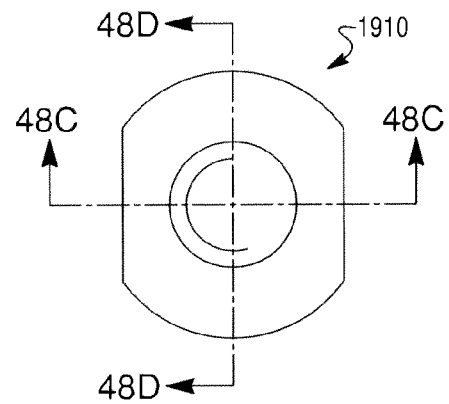
FIG. 48B is a top view of the low-profile, uniplanar bone screw of FIG. 48A.
Figure 48C:
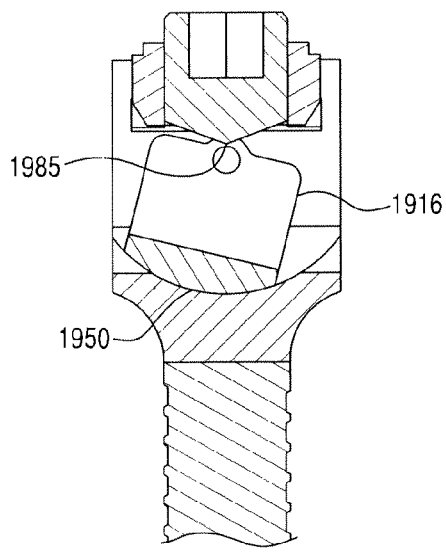
FIG. 48C is a cross-sectional view of the low-profile, uniplanar bone screw of FIG. 48B taken along line 48C-48C.
Figure 48D:
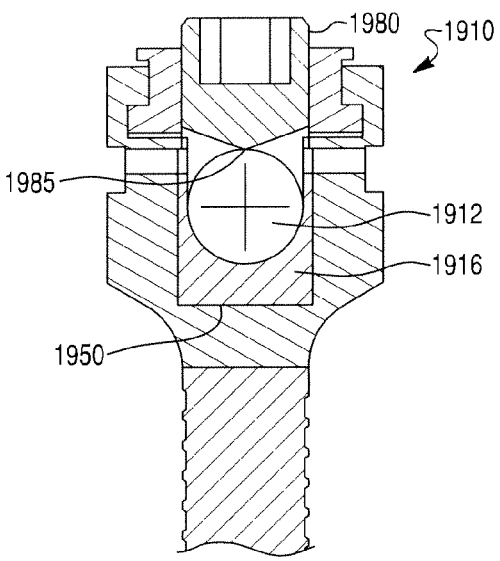
FIG. 48D is a cross-sectional view of the low-profile, uniplanar bone screw of FIG. 48B taken along line 48D-48D.
Figure 49A:
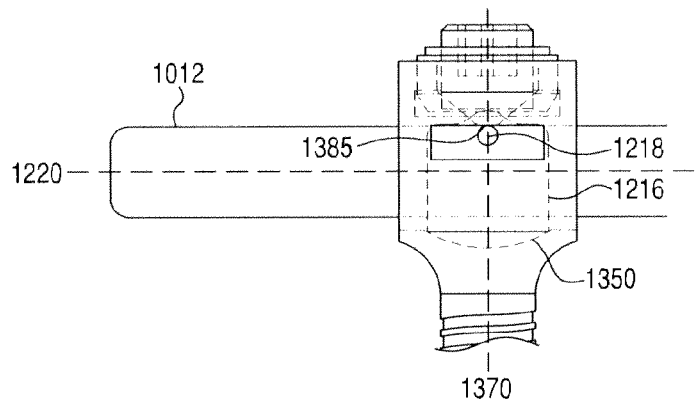
FIG. 49A is a side plan view of a low-profile, uniplanar bone screw.
Figure 49B:
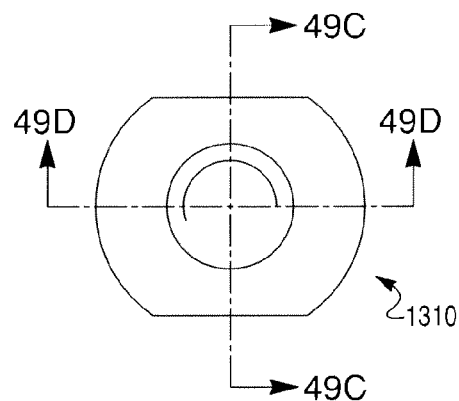
FIG. 49B is a top view of the low-profile, uniplanar bone screw of FIG. 49A.
Figure 49C:
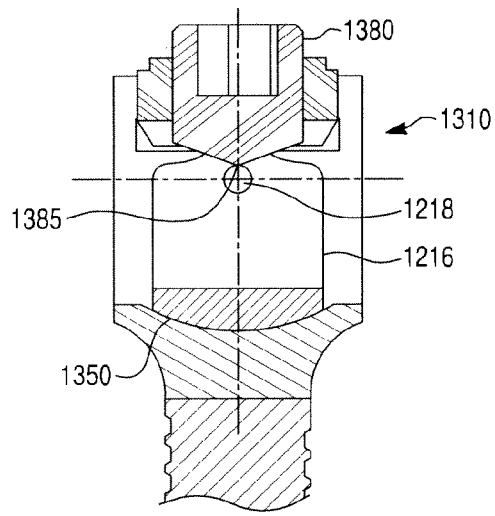
FIG. 49C is a cross-sectional view of the low-profile, uniplanar bone screw of FIG. 49B taken along line 49C-49C.
Figure 49D:
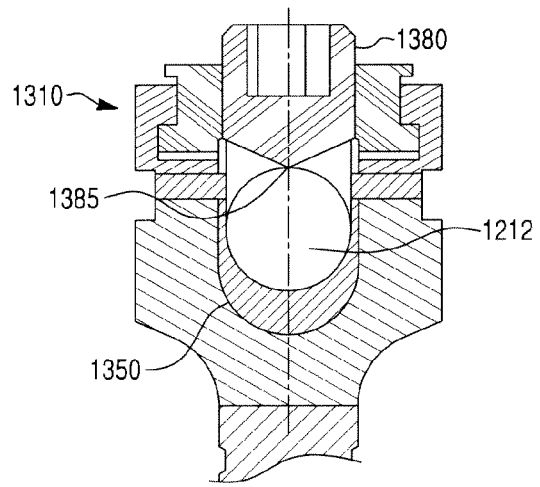
FIG. 49D is a cross-sectional view of the low-profile, uniplanar bone screw of FIG. 49B taken along line 49D-49D.
Figure 50A:
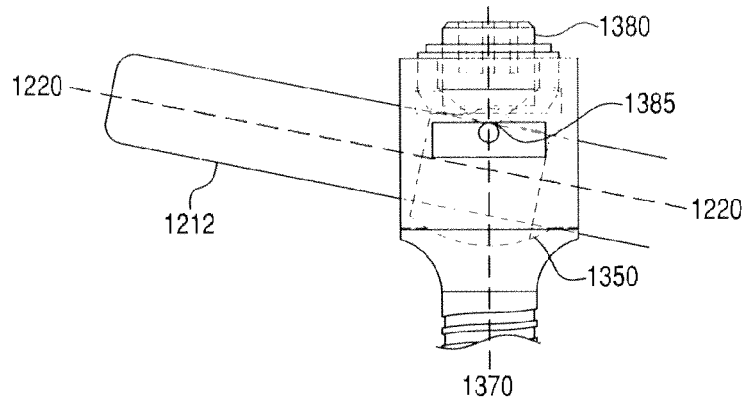
FIG. 50A is a side plan view of a low-profile, uniplanar bone screw.
Figure 50B:
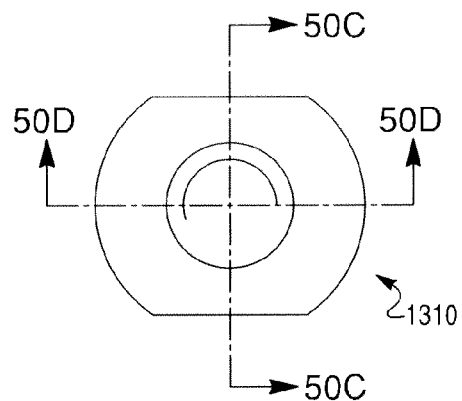
FIG. 50B is a top view of the low-profile, uniplanar bone screw of FIG. 50A.
Figure 50C:
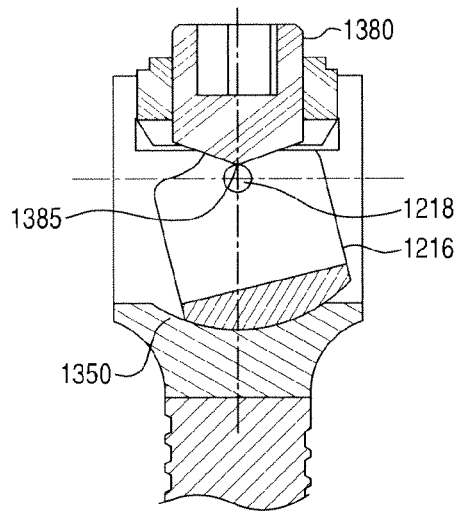
FIG. 50C is a cross-sectional view of the low-profile, uniplanar bone screw of FIG. 50 B taken along line 50C-50C.
Figure 50D:
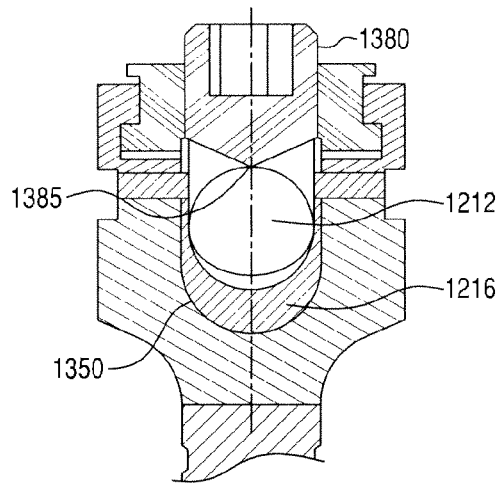
FIG. 50D is a cross-sectional view of the low-profile, uniplanar bone screw of FIG. 50B taken along line 50D-50D.

The fulcrum of the bone screw may be spaced a distance from a top surface of the swing hole or may be in line with a top surface of the swing hole. As shown in FIG. 46C, a top surface 1823 of the swing hole 1818 may be spaced a distance from the fulcrum 1885 of the rod-securing element 1880 such that the rod 1812 can move in a direction parallel to the longitudinal axis of the fulcrum 1885. In contrast, as shown in FIG. 47C, a top surface 1923 of the swing hole 1918 may be in line with a top surface 1923 of the swing hole 1918 such that the rod 1912 can not move in a direction parallel to the longitudinal axis of the fulcrum. Alternatively, the diameter of the swing hole 1918 may be larger than the diameter of the projection that fits within the swing hole 1918 so that the swing can move in a direction parallel to the longitudinal axis of the fulcrum. When the diameter of the swing hole 1918 is substantially equal to the diameter of the projection that fits within the swing hole 1918, the swing cannot move in a direction parallel to the longitudinal axis of the fulcrum. Both the swing hole 1818 and swing hole 1918 serve as an axis of rotation about which the swing rotates. Alternatively, the projection that fits within the swing hole may serve as an axis of rotation about which the swing rotates. When the rod-securing element is secured, the swing may contact the bottom surface of the slot such that a load is distributed and/or the swing may translate (e.g. move in a direction parallel to the longitudinal axis of the fulcrum).

Figure 51:
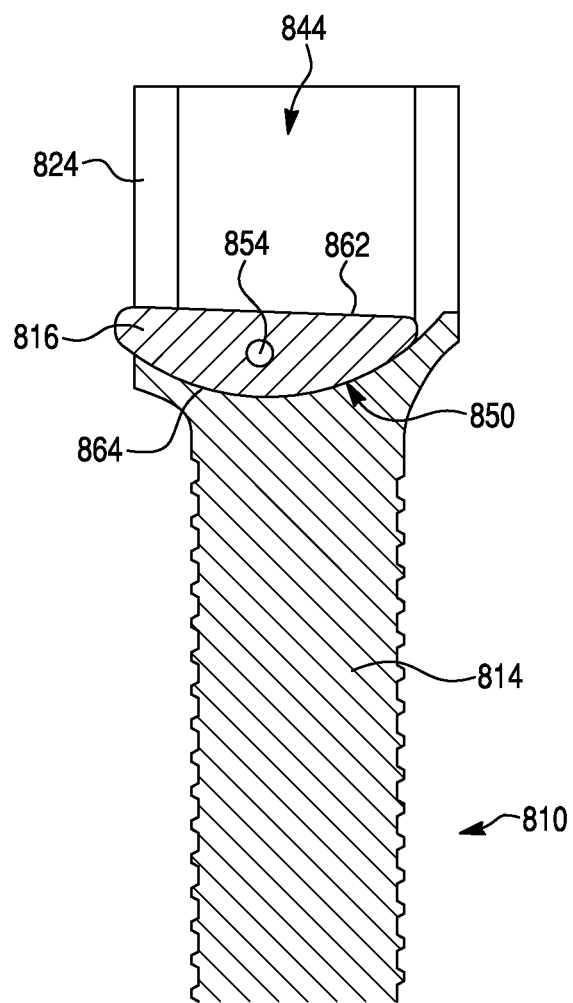
FIG. 51 is a cross sectional view of a low-profile uniplanar bone screw with an asymmetric slot.

Referring to FIG. 51, a low-profile bone screw 810 is shown. The bone screw 810 includes a main body 814, a head 824 and a slot 844. The bone screw 710 is shown substantially similar to bone screw 410 except that a bottom curved surface 850 of the slot 844 is asymmetric. In some cases, spinal curvatures (e.g., lordosis and kyphosis) have a larger curve than can be accommodated in other screws. The bottom surface 850 of the slot 844 is asymmetrical so as to offer greater angulations of the sliding rod support 816 in one direction.

The sliding rod support 816 for bone screw 810 includes an upper surface 862 and a bottom curved surface 864. The upper surface 862 is arranged to contact or interface with a rod. The bottom curved surface 864 contacts or interfaces with the bottom surface 850 of the slot 844. The sliding rod support 816 includes a projection 854 that is configured to be received within a corresponding guide feature (e.g., guide channel) (not shown) in the bone screw 810. The sliding rod support 816 may also have a groove or channel (e.g., guide channel) (not shown) to accept a projection 854 from the interior wall of the screw head 844.

Referring to FIGS. 52A-54C, a reduction screw 910 is shown. The reduction screw 910 may be used in spinal deformity patients in which the rod 912 may be positioned away from the patient. The reduction screw 910 may also be used to realign misaligned vertebrae such as spondylolisthesis. The reduction screw 910 includes a main body 914, a rocker 916 coupled to and movable relative to the main body 914 and that is configured to at least partially receive the rod 912 and a rod-securing element 18 configured to secure the rod 912 relative to the main body 914. The rocker 916 is a sliding rod support. The rod-securing element 918 may be any suitable element, such as a set screw.

The main body 914 includes a shaft 922 and a screw head 924 coupled to the shaft 922. The screw head 924 includes a top portion 972, a bottom portion 973 and a slot 944. The top portion 972 is detachably coupled to the bottom portion 973. The shaft 922 includes a threaded portion having a plurality of threads (not shown). The threaded portion is configured to be at least partially received within a bore (hole, cavity, etc.) formed in a person's spine. The threads of the threaded portion are configured to threadably engage the bore to secure the main body 14 to the spine.

The rod 912 may be placed into the slot 944 of the main body 914 and the rod-securing element 918 may be reduced into the head 924 until the rod 912 is seated in the rocker 916. Once the rod 912 is seated in the rocker 916, the top portion 972 may be decoupled from the bottom portion 973 by any suitable mechanism. For example, the top portion 972 may be manually detached from the bottom portion 973. Alternatively, the top portion 972 may be detached from the bottom portion 973 by any suitable instrument.

FIGS. 52A-52C illustrate the reduction screw 910 when the rod 912 is first placed within the slot 944. FIGS. 53A-53C illustrate the reduction screw 910 after the rod-securing element 918 is reduced into the head 924 such that the rod 912 is seated in the rocker 916. FIGS. 54A-54C illustrate the reduction screw 910 after the top portion 972 is decoupled from the bottom portion 973. Although FIGS. 52A-54C show that the top portion 972 of the head 924 is not decoupled until the rod 912 is seated in the rocker 916, the top portion 972 may be decoupled before the rod 912 is seated in the rocker 916. The reduction screw 1910 is configured to function substantially the same way as bone screw 10. Unlike non-reduction screws, the reduction screw 910 allows for more space within the screw head 924 for the misaligned vertebrae to traverse relative to the rod, thereby allowing the misaligned vertebrae to be realigned. For example, the reduction screw 910 may be at least partially screwed into a patient's vertebrae. Then the rod 912 may be placed into the slot 944 of the main body 914. A top surface of the rod 912 may abut the fulcrum of the rod-securing element 918 when the rod 912 is placed into the slot 944. Once placed in the slot 944, the rod-securing element 918 may be screwed into the slot 944. As the rod-securing element 918 is screwed into the slot, the rod 912 moves toward the rocker 916. As the rod 912 moves toward the rocker, the misaligned vertebrae moves toward the rod 912 so that the misaligned vertebrae can be realigned.

In all embodiments, the surface of the rocker can be textured to increase friction and thus prevent the rod from sliding in the direction of the rod axis. The surfaces of the rocker may be textured by etching or grit blasting.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature. For the purpose of this disclosure, the term "between" does not require direct connect between surfaces.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of the low-profile uniplanar bone screw or components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

What is claimed is:

1. A uniplanar bone screw for adjusting a position of a rod, comprising: a main body having a shaft with a threaded part; a rocker coupled to and moveable relative to the main body, wherein the rocker is configured to at least partially receive the rod; a rod-securing element configured to secure the rod between the rocker and the rod-securing element and relative to the main body, wherein the rod-securing element includes a fulcrum serving as an axis of rotation about which the rod rotates, wherein the rod-securing element comprises a screw directly abuts the rod, wherein the main body includes a screw head coupled to the shaft, wherein the screw head includes a slot configured to at least partially receive the rod and the rocker; and a guide feature in one of the slot and the rocker and a guide channel in the other of the slot and the rocker, wherein the guide channel is configured to receive the guide feature to guide movement of the rocker relative to the main body.

2. The uniplanar bone screw of claim 1, wherein the threaded portion is configured to at least partially be received within a spine.

3. The uniplanar bone screw of claim 1, wherein the guide feature comprises a projection.

4. The uniplanar bone screw of claim 1, wherein the slot includes a first interior sidewall and a second interior sidewall and a bottom surface that extends from the first interior sidewall to the second interior sidewall.

5. The uniplanar bone screw of claim 4, wherein the bottom surface of the slot supports the rocker.

6. The uniplanar bone screw of claim 4, wherein the bottom surface of the slot and a surface of the rocker each include substantially elongated surfaces configured to facilitate translational movement of the rocker relative to the main body.

7. The uniplanar bone screw of claim 4,
wherein the bottom surface of the slot is one of:
(i) substantially flat in a first direction and in a second direction,
(ii) substantially curved in the first direction and in the second direction,
(ii) substantially flat in the first direction and substantially curved in the second direction, and
(iv) substantially curved in the first direction and substantially flat in the second direction, and
wherein the second direction is substantially perpendicular to the first direction.

8. The uniplanar bone screw of claim 4, wherein the bottom surface of the slot includes a pointed portion.

9. The uniplanar bone screw of claim 1, wherein the rocker includes a taper that contacts the rod.

10. The uniplanar bone screw of claim 1, wherein the rocker includes an upper portion and wherein the upper portion includes a surface that is configured to interface with and at least partially support the rod.

11. The uniplanar bone screw of claim 1,
wherein the rocker includes a substantially elliptic portion, a first wing extending from a first end of the substantially elliptic portion and a second wing extending from a second end of the substantially elliptic portion, and
wherein the substantially elliptic portion, the first wing and the second wing are configured to confine the rocker within the main body.

12. The uniplanar bone screw of claim 1, wherein the rocker comprises one of a sliding rod support and a swing.

13. The uniplanar bone screw of claim 12, wherein the shape of the sliding rod support is one of substantially convex and substantially concave.

14. The uniplanar bone screw of claim 12, wherein the swing includes holes for receiving guide features that are configured to couple the swing to the main body.

15. The uniplanar bone screw of claim 12, wherein the swing includes one or more suspension lines that suspend the swing from the main body.

16. The uniplanar bone screw of claim 12, wherein the center of the sliding rod support serves as an axis of rotation about which the sliding rod support rotates.

17. The uniplanar bone screw of claim 12, wherein one of a swing hole of the swing and a projection serve as an axis of rotation about which the swing rotates.

18. The uniplanar bone screw of claim 12, wherein when the rod-securing element is secured, the swing at least one of contacts a bottom surface of a slot of the main body such that a load is distributed and translates.

19. The uniplanar bone screw of claim 1, wherein the se lead includes a bottom portion and a top portion that is detachably coupled to the bottom portion.

20. The uniplanar bone screw of claim 1, wherein the rocker is configured to at least one of translate and rotate within the slot.

21. The uniplanar bone screw of claim 1, wherein an angle of rotation of the rod is determined by the distance of the center of the rocker from the fulcrum of the rod-securing element.

22. The uniplanar bone screw of claim 1, wherein the fulcrum comprises a cone-shape and a pointed portion of the cone directly abuts the rod.

* * * * *

UNITED STATES PATENT AND TRADEMARK OFFICE
CERTIFICATE OF CORRECTION

PATENT NO.       : 9,277,950 B2
APPLICATION NO.  : 13/702854
DATED            : March 8, 2016
INVENTOR(S)      : Glenn R. Buttermann It is certified that error appears in the above-identified patent and that said Letters Patent is hereby corrected as shown below:

In the Claims

Column 18, Claim 19, lines 1 and 2, "The uniplanar bone screw of claim 1, wherein the se lead" should read:

--The uniplanar bone screw of claim 1, wherein the screw head--.

Signed and Sealed this
Fourteenth Day of June, 2016

Michelle K. Lee
*Director of the United States Patent and Trademark Office*